(12) United States Patent
Hagiwara et al.

(10) Patent No.: US 11,318,126 B2
(45) Date of Patent: May 3, 2022

(54) COMPOSITION FOR ACTIVATING NEUROGENESIS

(71) Applicant: KYOTO UNIVERSITY, Kyoto (JP)

(72) Inventors: Masatoshi Hagiwara, Kyoto (JP); Akiko Kobayashi, Kyoto (JP); Takamitsu Hosoya, Tokyo (JP); Suguru Yoshida, Tokyo (JP); Yuto Sumida, Tokyo (JP)

(73) Assignee: Kyoto University, Kyoto (JP)

( * ) Notice: Subject to any disclaimer, the term of this patent is extended or adjusted under 35 U.S.C. 154(b) by 89 days.

(21) Appl. No.: 16/329,063

(22) PCT Filed: Aug. 31, 2017

(86) PCT No.: PCT/JP2017/031453
§ 371 (c)(1),
(2) Date: Apr. 30, 2019

(87) PCT Pub. No.: WO2018/043674
PCT Pub. Date: Mar. 8, 2018

(65) Prior Publication Data
US 2019/0247384 A1    Aug. 15, 2019

(30) Foreign Application Priority Data

Aug. 31, 2016    (JP) .............................. JP2016-170168

(51) Int. Cl.
| | | |
|---|---|---|
| *A61K 31/47* | (2006.01) | |
| *A61K 31/443* | (2006.01) | |
| *A61P 43/00* | (2006.01) | |
| *A61P 25/24* | (2006.01) | |
| *A61K 31/4709* | (2006.01) | |
| *A61P 25/16* | (2006.01) | |
| *A61K 45/00* | (2006.01) | |
| *A61P 25/14* | (2006.01) | |
| *A61P 25/02* | (2006.01) | |
| *A61K 31/4439* | (2006.01) | |
| *A61K 31/4725* | (2006.01) | |
| *A61P 25/28* | (2006.01) | |
| *A61P 25/00* | (2006.01) | |
| *A61K 31/416* | (2006.01) | |
| *C12N 5/0793* | (2010.01) | |

(52) U.S. Cl.
CPC ............ *A61K 31/47* (2013.01); *A61K 31/416* (2013.01); *A61K 31/443* (2013.01); *A61K 31/4439* (2013.01); *A61K 31/4709* (2013.01); *A61K 31/4725* (2013.01); *A61K 45/00* (2013.01); *A61P 25/00* (2018.01); *A61P 25/02* (2018.01); *A61P 25/14* (2018.01); *A61P 25/16* (2018.01); *A61P 25/24* (2018.01); *A61P 25/28* (2018.01); *A61P 43/00* (2018.01); *C12N 5/0619* (2013.01)

(58) Field of Classification Search
USPC ......................................................... 514/313
See application file for complete search history.

(56) References Cited

U.S. PATENT DOCUMENTS

| | | | |
|---|---|---|---|
| 6,379,666 B1 * | 4/2002 | Tobinick | ............... C07K 16/241 424/134.1 |
| 2007/0282101 A1 | 12/2007 | Ericsson et al. | |
| 2011/0136844 A1 | 6/2011 | Sheherbakova et al. | |
| 2016/0303089 A1 | 10/2016 | Hagiwara et al. | |

FOREIGN PATENT DOCUMENTS

| | | |
|---|---|---|
| JP | 2009-292782 A | 12/2009 |
| JP | 2009-544631 A | 12/2009 |
| JP | 2010-105996 A | 5/2010 |
| WO | WO 2007/117465 A2 | 10/2007 |
| WO | WO 2008/014602 A1 | 2/2008 |
| WO | WO 2014/069434 A1 | 5/2014 |
| WO | WO 2015/083750 A1 | 6/2015 |

OTHER PUBLICATIONS

Kobayaski (Prenatal neurogenesis induction therapy normalizes brain structure and function in Down syndrome mice, PNAS | Sep. 19, 2017 | vol. 114 | No. 38).*
Coombs et al., "Small-molecule pyrimidine inhibitors of the cdc2-like (CJk) and dual specificity tyrosine phosphorylation-regulated (Dyrk) kinases: Development of chemical probe ML315", Bioorganic & Medicinal Chemistry Letters, 2013, vol. 23, No. 12, pp. 3654-3661.
International Search Report (PCT/ISA/210) issued in PCT/JP2017/031453, dated Oct. 10, 2017.
Meijer et al., "Leucettines, A Class of Dyrks/Clks Dual Inhibitors: Implications for Treatment of Alzheimer's Disease and Down Syndrome", Neurodegener Dis, 2015, vol. 15, Suppl 1, p. 722, Abstract No. ADPD5-0394, entire text.

(Continued)

*Primary Examiner* — Kathrien A Cruz
(74) *Attorney, Agent, or Firm* — Birch, Stewart, Kolasch & Birch, LLP

(57) ABSTRACT

Provided is a composition for activating neurogenesis, use of the composition, and a method for preventing, improving, inhibiting the development of, and/or treating a disease or the like of the central nervous system and or the peripheral nervous system using the composition. A composition for activating neurogenesis contains, as an active ingredient, a compound having an ability to inhibit phosphorylation activity of a protein kinase or a prodrug thereof, or a pharmaceutically acceptable salt thereof, and a composition for preventing, improving, inhibiting the development of, and/or treating a disease of the central nervous system and/or the peripheral nervous system, or for improving, inhibiting the development of, and/or treating a functional disorder of the central nervous system and/or the peripheral nervous system, the composition containing, as an active ingredient, a compound having an ability to inhibit phosphorylation activity of a protein kinase or a prodrug thereof, or a pharmaceutically acceptable salt thereof.

3 Claims, 6 Drawing Sheets

(56) References Cited

OTHER PUBLICATIONS

Muraki et al., "Manipulation of Alternative Splicing by a Newly Developed Inhibitor of Clks", The Journal of Biological Chemistry, 2004, vol. 279, No. 23, pp. 24246-24254.
Ohe et al., "Modulation of Alternative Splicing with Chemical Compounds in New Therapeutics for Human Diseases", ACS Chem. Biol., 2015, vol. 10, pp. 914-924.
Duchon et al., "DYRK1A, a Dosage-Sensitive Gene Involved in Neurodevelopmental Disorders, Is a Target for Drug Development in Down Syndrome," Frontiers in Behavioral Neuroscience, vol. 10, Article 104, May 3, 2016, pp. 1-17.
European Patent Office Communication and extended search report issued in the corresponding European Patent Application No. 17846678.5 dated Mar. 31, 2020.
European Communication pursuant to Article 94(3) EPC for European Application No. 17846678.5, dated Feb. 2, 2021.

\* cited by examiner

A Paralysis score

| score | 0 | 1 | 2 | 3 |
|---|---|---|---|---|
| Nictitation | Incapable of opening Eye | Incapable of fully opening eye | Asymmetric | Cured |
| Nose | Extension | Slight extension | Asymmetric | Cured |
| Whisker | Incapable of moving | Capable of moving | Asymmetric | Cured |

COMPOSITION FOR ACTIVATING NEUROGENESIS

TECHNICAL FIELD

The present disclosure relates to a composition for activating neurogenesis, and a composition for treatment or the like of a disease or functional disorder of the central nervous system and/or the peripheral nervous system. The present disclosure also relates to use of the composition, a method for preventing, improving, inhibiting the development of, and/or treating a disease using the composition, a method for activating neurogenesis, and a method for activating the proliferation of nerve cells.

BACKGROUND ART

In recent years, it has been elucidated that neurogenesis and nerve regeneration can occur in the central nervous system. This facilitates development of drugs capable of controlling neurogenesis. Patent Document 1 discloses a neurogenesis promoter containing a peptide that can promote neurogenesis in the hippocampus of the brain of a mammal. Patent Document 2 discloses a low molecular weight compound having a neurogenic activity.

CITATION LIST

Patent Documents

Patent Document 1: JP 2010-105996A
Patent Document 2: JP 2009-292782A

DISCLOSURE OF INVENTION

Problem to be Solved by the Invention

An aspect of the present disclosure provides a composition for activating neurogenesis, use of the composition, and a method for preventing, improving, inhibiting the development of, and/or treating a disease using the composition.

Means for Solving Problem

An aspect of the present disclosure relates to a composition for activating neurogenesis containing, as an active ingredient, a compound having an ability to inhibit phosphorylation activity of a protein kinase or a prodrug thereof, or a pharmaceutically acceptable salt thereof.

Another aspect of the present disclosure relates to a composition for:
preventing, improving, inhibiting the development of, and/or treating a disease of the central nervous system and/or the peripheral nervous system, or
improving, inhibiting the development of, and/or treating a functional disorder of the central nervous system and/or the peripheral nervous system,
the composition contains, as an active ingredient, a compound having an ability to inhibit phosphorylation activity of a protein kinase or a prodrug thereof, or a pharmaceutically acceptable salt thereof.

Yet another aspect of the present disclosure relates to a composition for activating neurogenesis containing, as an active ingredient, a compound represented by formula (I) or a prodrug thereof, or a pharmaceutically acceptable salt thereof:

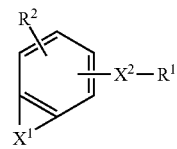

(I)

where $X^1$ is

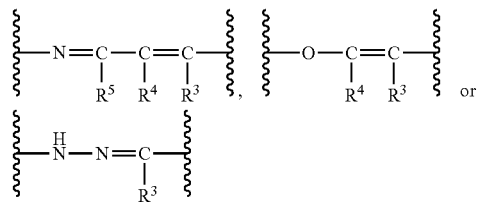

where $R^3$, $R^4$, and $R^5$ are independently a hydrogen atom, a halogen atom, a carboxyl group, an amino group, a hydroxyl group, a $C_{1-4}$ alkyl group, or a halogen-substituted $C_{1-4}$ alkyl group;

$X^2$ is -(bond) or —NH—;

$R^1$ is

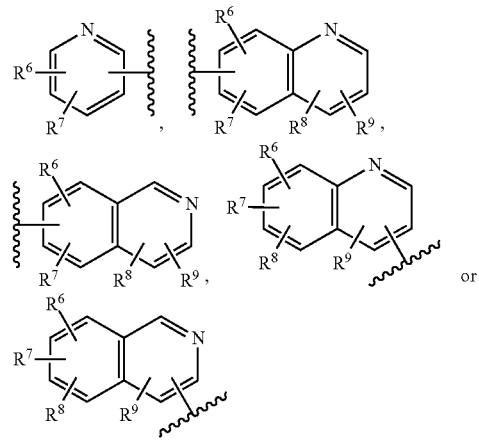

where $R^6$, $R^7$, $R^8$, and $R^9$ are independently a hydrogen atom, a halogen atom, a carboxyl group, an amino group, a hydroxyl group, a $C_{1-4}$ alkyl group, or a halogen-substituted $C_{1-4}$ alkyl group; and $R^2$ is a hydrogen atom, a halogen atom, a carboxyl group, an amino group, a hydroxyl group, a $C_{1-4}$ alkyl group, or a halogen-substituted $C_{1-4}$ alkyl group.

Yet another aspect of the present disclosure relates to a composition for:
preventing, improving, inhibiting the development of, and/or treating a disease of the central nervous system and/or the peripheral nervous system, or
improving, inhibiting the development of, and/or treating a functional disorder of the central nervous system and/or the peripheral nervous system,
wherein the composition contains, as an active ingredient, a compound represented by formula (I) or a prodrug thereof, or a pharmaceutically acceptable salt thereof.

Yet another aspect of the present disclosure relates to a method for:

preventing, improving, inhibiting the development of, and/or treating a disease of the central nervous system and/or the peripheral nervous system, or improving, inhibiting the development of, and/or treating a functional disorder of the central nervous system and/or the peripheral nervous system, wherein the method includes administering the composition of the present disclosure to a subject.

Yet another aspect of the present disclosure relates to use of a compound for producing a pharmaceutical composition, wherein the pharmaceutical composition for use in;

preventing, improving, inhibiting the development of, and/or treating a disease of the central nervous system and/or the peripheral nervous system, or improving, inhibiting the development of, and/or treating a functional disorder of the central nervous system and/or the peripheral nervous system, wherein the compound is represented by formula W or a prodrug thereof, or a pharmaceutically acceptable salt thereof.

Yet another aspect of the present disclosure relates to use of a compound represented by formula (I) or a prodrug thereof, or a pharmaceutically acceptable salt thereof to activate neurogenesis.

BRIEF DESCRIPTION OF DRAWINGS

FIG. 8A shows examples of the results of Y maze test for spontaneous alteration behavior, FIG. 8B shows examples of the results of Barnes maze test for spatial memory, and FIG. 8C shows examples of the results of fear conditioning test.

DESCRIPTION OF THE INVENTION

Figure 1:
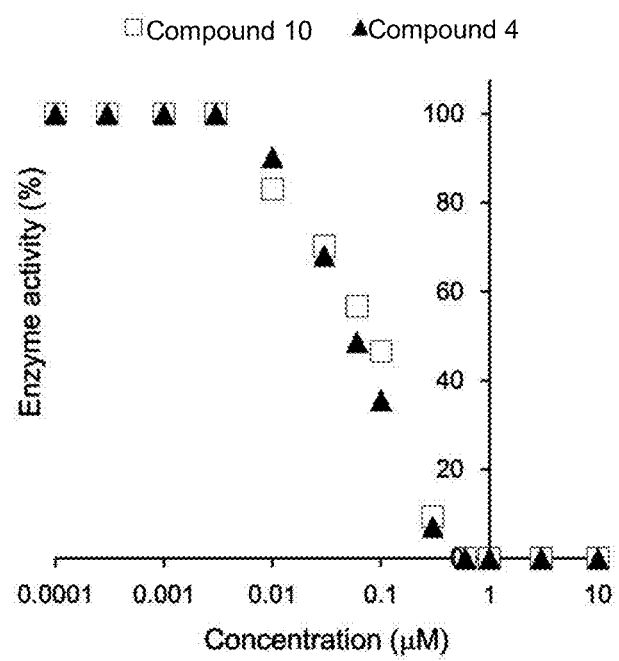
FIG. 1 is an example of the results of in-vitro kinase assay showing the inhibitory activity of Compound 4 or 10 against Dual-specificity tyrosine phosphorylation-regulated kinase 1A (DYRK1A).

It is reported that the expression level of a protein kinase increases in the brains of Down syndrome patients and Down syndrome model mice. It is also reported that a decrease in neurogenesis is observed in Down syndrome model mice. Accordingly, the inventors of the present invention investigated whether an inhibitor that controls the phosphorylation activity of a protein kinase can be used to suppress the decrease in neurogenesis and to provide a drug against a disease or functional disorder of the central/peripheral nervous systems such as Down syndrome. During the investigation, the inventors of the present invention found that a compound having inhibitory activity against the phosphorylation activity of a protein kinase suppresses the phosphorylation of tau protein, promotes the proliferation of neural stem cells, and stimulates the progression of the cell cycle from the G1 phase to the subsequent S phase and G2/M phase by stabilizing cyclin D1.

An aspect of the present disclosure is based on the finding that a compound represented by formula (I) has inhibitory activity against the phosphorylation activity of a protein kinase belonging to the Dual-specificity tyrosine phosphorylation-regulated kinase (DYRK) family.

An aspect of the present disclosure is based on the finding that the compound represented by formula (i) has a function of suppressing the phosphorylation of tau protein.

An aspect of the present disclosure is based on the finding that the compound represented by formula (I) promotes the proliferation of neural stem cells.

An aspect of the present disclosure is based on the finding that the compound represented by formula (I) increases the expression level of cyclin D1, and further stimulates the progression of the cell cycle from the G1 phase to the subsequent S phase and G2/M phase.

An aspect of the present disclosure is based on the finding that the compound represented by formula (I) can be used to prevent, improve, inhibit the development of, and/or treat a central neurological disease such as Down syndrome caused by a decrease in neurogenesis.

An aspect of the present disclosure is based on the finding that the compound represented by formula (I) can be used to prevent, improve, inhibit the development of, and/or treat a peripheral neurological disease such as facial palsy.

An aspect of the present disclosure is based on the finding that the compound represented by formula (I) can be used to improve, inhibit the development of, and/or treat a functional disorder of the central/peripheral nervous systems such as a spinal cord injury.

Activation of Neurogenesis

An aspect of the present disclosure relates to a composition for activating neurogenesis containing, as an active ingredient, a compound having an ability to inhibit the phosphorylation activity of a protein kinase or a prodrug thereof, or a pharmaceutically acceptable salt.

In one or more embodiments, the term "neurogenesis" as used in the present disclosure means the division and proliferation of neural stem cells in an organism or an adult, the production of neural precursor cells, the differentiation and maturation of produced neural precursor cells to nerve cells, or a combination thereof. Examples of the organism or adult include a mammal, a human, and a non-human mammal. The term "neural stem cells" as used in the present disclosure means cells that reside in the brain and spinal cord and produce precursor cells having an ability to differentiate into nerve cells or glia cells. In one or more embodiments, the term "activation of neurogenesis" as used in the present disclosure means enhancement of the division and proliferation of neural stem cells in an organism or an adult, the production of neural precursor cells, the differentiation and maturation of produced neural precursor cells to nerve cells, or a combination thereof. In one or more embodiments, the term "activation of neurogenesis" may encompass mitigating decreased neurogenesis or increasing neurogenesis.

In one or more embodiments, examples of the compound having an ability to inhibit the phosphorylation activity of a protein kinase include a compound having an ability to inhibit the phosphorylation activity of a protein kinase belonging to the DYRK family, a compound having an ability to inhibit the phosphorylation activity of a protein kinase belonging to the CLK family, a compound having an ability to inhibit the phosphorylation activity of a kinase that phosphorylates cyclin D1, a compound having an ability to suppress the abnormal phosphorylation of tau protein, and a compound having both inhibiting and suppressing abilities. In one or more embodiments, examples of the protein kinase belonging to the DYRK family include DYRK1A, DYRK2, DYRK1B, and DYRK3. In one or more embodiments, examples of the protein kinase belonging to the CLK family include CLK1 and CLK2. In one or more embodiments, examples of the kinase that phosphorylates cyclin D1 include protein kinases belonging to the DYRK family and glycogen synthase kinase 3β (GSK3β).

In one or more embodiments that are not particularly limited, an example of the compound having an ability to inhibit the phosphorylation activity of the above-mentioned protein kinase is a compound represented by formula (I) or a prodrug thereof, or a pharmaceutically acceptable salt thereof (compound according to the present disclosure).

In one or more embodiments, the composition according to the present disclosure can be used as a pharmaceutical composition for activating neurogenesis. Accordingly, in one or more embodiments, the composition according to the present disclosure can be administered to a subject to prevent, improve, inhibit the development of, or treat a disease of the central nervous system or peripheral nervous system. In one or more embodiments, the composition according to the present disclosure can be administered to a subject to improve, inhibit the development of, and/or treat a functional disorder of the central nervous system or peripheral nervous system.

Treatment or the like of disease or functional disorder of central/peripheral nervous systems Another aspect of the present disclosure relates to a composition and a pharmaceutical composition for preventing, improving, inhibiting the development of, and/or treating a disease of the central nervous system and/or the peripheral nervous system, or for improving, inhibiting the development of, and/or treating a functional disorder of the central nervous system and/or the peripheral nervous system, the compositions containing, as an active ingredient, a compound having an ability to inhibit the phosphorylation activity of a protein kinase or a prodrug thereof, or a pharmaceutically acceptable salt thereof.

In one or more embodiments, examples of a central neurological disease include diseases with symptoms relating to the functions of the brain or spinal cord in which a large number of nerve cells are concentrated. In one or more embodiments, the disease or functional disorder of the central nervous system or the peripheral nervous system is a disease or functional disorder caused by atrophy of the hippocampus, and examples thereof include intellectual disabilities, learning disabilities, mood disorders, PTSD, anxiety disorders, organic mental disorders including symptomatic mental disorders, and substance-related disorders (particularly alcohol-related disorders and stimulator-related disorders). In one or more embodiments, examples of the central neurological disease include mental diseases such as Down syndrome, Alzheimer's disease, Parkinson's disease, Huntington's disease, and Alzheimer's disease that may occur in Down syndrome patients. In one or more embodiments, examples of the peripheral neurological disease include glossopharyngeal nerve disorders such as facial palsy and sudden paralysis, and trigeminal nerve disorders. In one or more embodiments, examples of the neurological functional disorder include neurological functional disorders following a stroke and cerebrospinal injury. In one or more embodiments, examples of the disease or functional disorder to be targeted by the composition and the pharmaceutical composition according to the present disclosure include a cerebral infarction, a spinal infarction, a cerebral hemorrhage, a spinal hemorrhage, facial palsy, quadriplegia, a neurodegenerative disease, Alzheimer's disease, Down syndrome, depression, Parkinson's disease, and Huntington's disease.

That is, the present disclosure may relate to one or more embodiments.

[A1] A composition for activating neurogenesis containing, as an active ingredient, a compound having an ability to inhibit phosphorylation activity of a protein kinase or a prodrug thereof, or a pharmaceutically acceptable salt thereof.

[A2] A composition for preventing, improving, inhibiting the development of, and/or treating a disease of the central nervous system and/or the peripheral nervous system, or for improving, inhibiting the development of, and/or treating a functional disorder of the central nervous system and/or the peripheral nervous system, the composition containing, as an active ingredient, a compound having an ability to inhibit phosphorylation activity of a protein kinase or a prodrug thereof, or a pharmaceutically acceptable salt thereof.

[A3] The composition according to [A2], wherein the compound activates neurogenesis.

[A4] The composition according to any one of [A1] to [A3], wherein the protein kinase is selected from the group consisting of CLK, DYRK, and a cyclin D1 kinase.

[A5] The composition according to any one of [A1] to [A4], wherein the compound is selected from the group consisting of a compound having an ability to inhibit phosphorylation activity of a protein kinase belonging to the DYRK family, a compound having an ability to inhibit phosphorylation activity of a protein kinase belonging to the CLK family, a compound having an ability to inhibit phosphorylation activity of a kinase that phosphorylates cyclin D1, a compound having an ability to suppress abnormal phosphorylation of tau protein, and a compound having both inhibiting and suppressing abilities.

[A6] The composition according to any one of [A2] to [A5], wherein the disease is selected from the group consisting of a cerebral infarction, a spinal infarction, a cerebral hemorrhage, a spinal hemorrhage, facial palsy, quadriplegia, a neurodegenerative disease, Alzheimer's disease, Down syndrome, depression, Parkinson's disease, and Huntington's disease.

[A7] The composition according to any one of [A1] to [A6], which is a pharmaceutical composition.

[A8] The pharmaceutical composition according to [A7] for preventing, improving, inhibiting the development of, and/or treating a disease of the central nervous system and/or the peripheral nervous system, or for improving, inhibiting the development of, and/or treating a functional disorder of the central nervous system and/or the peripheral nervous system.

Composition containing compound represented by formula (I) as active ingredient

In one or more embodiments, the compound represented by formula (I) has inhibitory activity against the phosphorylation activity of DYRK1A. In one or more embodiments, the compound represented by formula (I) also suppresses the abnormal phosphorylation of tau protein. In one or more embodiments, the compound represented by formula (I) also increases the expression level of cyclin D1 or stabilizes cyclin D1 in neural stem cells.

Accordingly, an aspect of the present disclosure relates to a DYRK inhibitor, an agent for suppressing the abnormal phosphorylation of tau protein, or an agent for stabilizing cyclin D1 in neural stem cells that contains, as an active ingredient, the compound represented by formula (I) or a prodrug thereof, or a pharmaceutically acceptable salt thereof.

In one or more embodiments, the compound represented by formula (I) enables at least one of the promotion of the proliferation of neural stem cells, the promotion of the neurogenesis in the dentate gyrus of the hippocampus, and the compensation for decreased proliferation of neural stem cells. In one or more embodiments, the compound represented by formula (I) is transported into the brain and is absorbed orally. Accordingly, in one or more embodiments, the compound represented by formula (I) can be used to prevent, improve, inhibit the development of, and treat diseases of the central nervous system and the peripheral nervous system. In one or more embodiments, the composition according to the present disclosure containing the compound represented by formula (I) as an active ingredient can be used to improve, inhibit the development of, and treat functional disorders of the central nervous system and the peripheral nervous system. The diseases or functional disorders of the central nervous system or the peripheral nervous system are as described above.

Compound represented by formula (I)

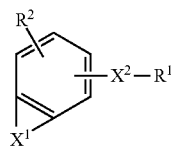

$X^1$ is

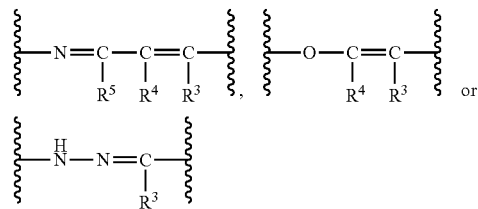

where $R^3$, $R^4$, and $R^5$ are independently a hydrogen atom, a halogen atom, a carboxyl group, an amino group, a hydroxyl group, a $C_{1-4}$ alkyl group, or a halogen-substituted $C_{1-4}$ alkyl group.

$X^2$ is -(bond) or —NH—.

$R^1$ is

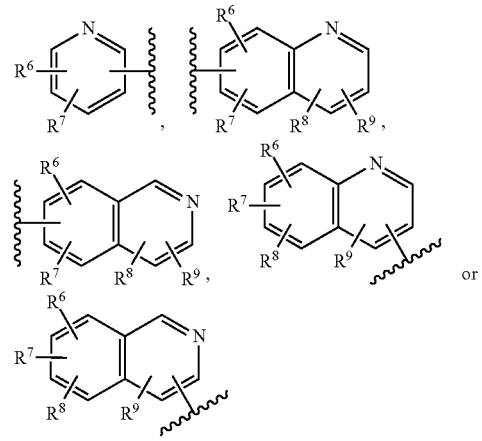

where $R^6$, $R^7$, $R^8$, and $R^9$ are independently a hydrogen atom, a halogen atom, a carboxyl group, an amino group, a hydroxyl group, a $C_{1-4}$ alkyl group, or a halogen-substituted $C_{1-4}$ alkyl group.

$R^2$ is a hydrogen atom, a halogen atom, a carboxyl group, an amino group, a hydroxyl group, a $C_{1-4}$ alkyl group, or a halogen-substituted $C_{1-4}$ alkyl group.

It should be noted that bonds with a wavy line indicate portions linked to formula (I) in the present disclosure.

In one or more embodiments, $R^2$, $R^3$, $R^4$, $R^5$, $R^6$, $R^7$, $R^8$, and $R^9$ in formula (I) are independently a hydrogen atom, a halogen atom, a $C_{1-4}$ alkyl group, or a halogen-substituted $C_{1-4}$ alkyl group.

In the present disclosure, examples of the $C_{1-4}$ alkyl group include a methyl group, an ethyl group, a propyl group, an isopropyl group, an n-butyl group, an isobutyl group, a sec-butyl group, and a tert-butyl group. In the present disclosure, the halogen-substituted $C_{1-4}$ alkyl group is a $C_{1-4}$ alkyl group in which one or more hydrogen atoms are substituted with a halogen atom. In the present disclosure, examples of the halogen atom include a fluorine atom, a chlorine atom, a bromine atom, and an iodine atom.

In one or more embodiments of the present disclosure, the compound represented by formula (I) is

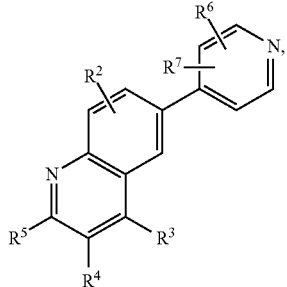

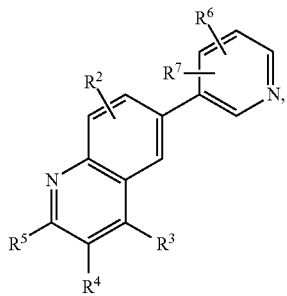

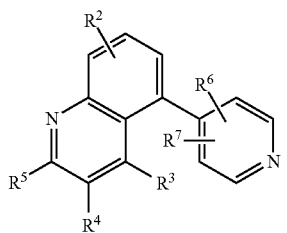

or

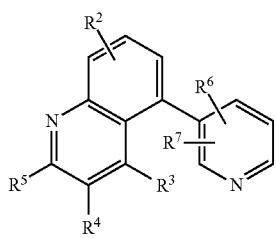

where $R^2$, $R^3$, $R^4$, $R^5$, $R^6$, and $R^7$ are as described above.

In one or more embodiments of the present disclosure, the compound represented by formula (I) is

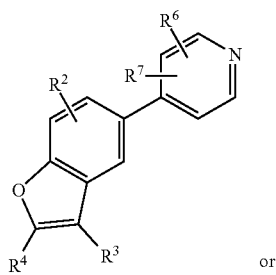 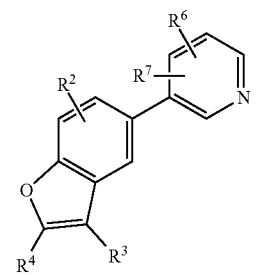

where $R^2$, $R^3$, $R^4$, $R^6$, and $R^7$ are as described above.

In one or more embodiments of the present disclosure, the compound represented by formula (I) is

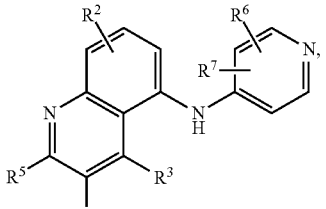

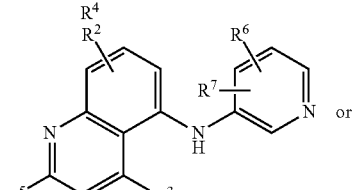

or

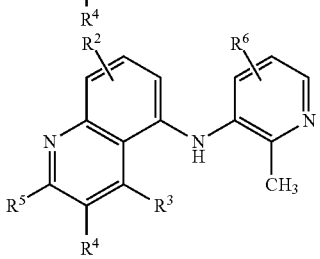

where $R^2$, $R^3$, $R^4$, $R^5$, $R^6$, and $R^7$ are as described above.

In one or more embodiments of the present disclosure, the compound represented by formula (I) is

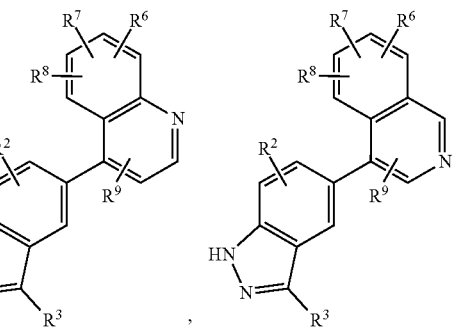

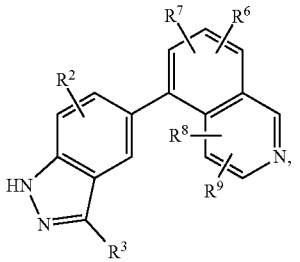

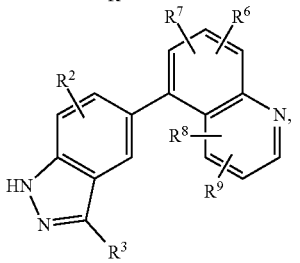

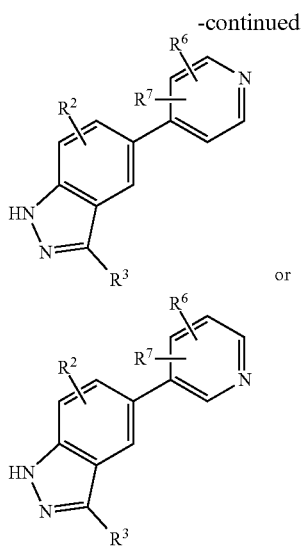

where $R^2$, $R^3$, $R^6$, $R^7$, $R^8$, and $R^9$ are as described above.

The term "pharmaceutically acceptable salt" as used in the present disclosure encompasses pharmacologically and/or medically acceptable salts, and examples thereof include inorganic acid salts, organic acid salts, inorganic base salts, organic base salts, and acidic or basic amino acid salts.

Preferable examples of the inorganic acid salts include hydrochlorides, hydrobromides, sulfates, nitrates, and phosphates. Preferable examples of the organic acid salts include acetates, succinates, fumarates, maleates, tartrates, citrates, lactates, stearates, benzoates, methanesulfonates, and p-toluenesulfonates.

Preferable examples of the inorganic base salts include alkali metal salts such as sodium salts and potassium salts, alkali earth metal salts such as calcium salts and magnesium salts, aluminum salts, and ammonium salts. Preferable examples of the organic base salts include diethylamine salts, diethanolamine salts, meglumine salts, and N,N'-dibenzylethylenediamine salts.

Preferable examples of the acidic amino acid salts include aspartates and glutamates. Preferable examples of the basic amino acid salts include argininates, lysinates, and ornithinates.

The term "salts of compounds" as used in the present disclosure may encompass hydrates that may be formed due to the compounds absorbing moisture while being left out in the air. Also, the term "salts of compounds" as used in the present disclosure may encompass solvates that may be formed due to the compounds absorbing another certain type of solvent.

In one or more embodiments, the term "prodrug" as used in the present disclosure means a compound that is converted into the compound represented by formula (I) in an organism. Examples of the prodrug of a compound having a carboxyl group include a compound having an alkoxycarbonyl group instead of the carboxyl group, a compound having an alkylthiocarbonyl group instead of the carboxyl group, and a compound having an alkylaminocarbonyl group instead of the carboxyl group. Examples of the prodrug of a compound having an amino group include a compound having an alkanoylamino group obtained by subjecting the amino group to substitution using an alkanoyl group, a compound having an alkoxycarbonylamino group obtained by subjecting the amino group to substitution using an alkoxycarbonyl group, a compound having an acyloxymethylamino group instead of the amino group, and a compound having a hydroxylamine instead of the amino group. Examples of the prodrug of a compound having a hydroxyl group include a compound having an acyloxy group obtained by subjecting the hydroxyl group to substitution using an acyl group, a compound having a phosphate instead of the hydroxyl group, and a compound having an acyloxymethyloxy group instead of the hydroxyl group. Examples of the alkyl moiety of the group used to form these prodrugs include alkyl groups as described later, and the alkyl groups may be subjected to substitution (using an alkoxy group having 1 to 6 carbon atoms or the like, for example). In one or more embodiments, for example, the compound having an alkoxycarbonyl group instead of the carboxyl group has a lower alkoxycarbonyl (having 1 to 6 carbon atoms, for example) such as methoxycarbonyl or ethoxycarbonyl, a lower alkoxycarbonyl (having 1 to 6 carbon atoms, for example) subjected to substitution using an alkoxy group, such as methoxymethoxycarbonyl, ethoxyethoxycarbonyl, 2-methoxyethoxycarbonyl, 2-methoxyethoxymethoxycarbonyl, or pivaloyloxymethoxycarbonyl.

That is, the present disclosure may relate to one or more embodiments below.

[B1] A DYRK inhibitor containing, as an active ingredient, the compound represented by formula (I) or a prodrug thereof, or a pharmaceutically acceptable salt thereof.

[B2] An agent for suppressing abnormal phosphorylation of tau protein, the agent containing, as an active ingredient, the compound represented by formula (I) or a prodrug thereof, or a pharmaceutically acceptable salt thereof.

[B3] An agent for stabilizing cyclin D1 in neural stem cells, the agent containing, as an active ingredient, the compound represented by formula (I) or a prodrug thereof, or a pharmaceutically acceptable salt thereof.

[B4] A composition for activating neurogenesis containing, as an active ingredient, the compound represented by formula (I) or a prodrug thereof, or a pharmaceutically acceptable salt thereof. [B5] The composition according to any one of [B1] to [B4], wherein $R^2$, $R^3$, $R^4$, $R^5$, $R^6$, $R^7$, $R^8$, and $R^9$ in formula (I) are independently a hydrogen atom, a halogen atom, a $C_{1-4}$ alkyl group, or a halogen-substituted $C_{1-4}$ alkyl group.

[B6] The composition according to any one of [B1] to [B5], wherein the compound represented by formula (I) is

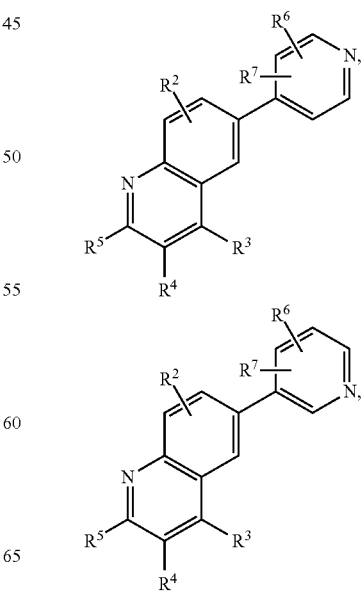

-continued
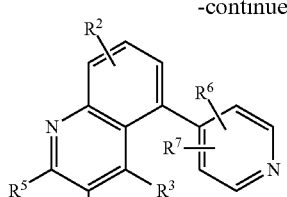
or
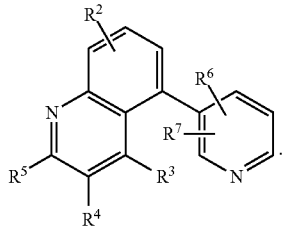
[B6] The composition according to any one of [B1] to [B5], wherein the compound represented by formula (I) is
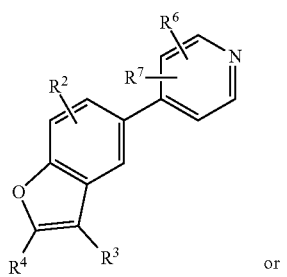
or
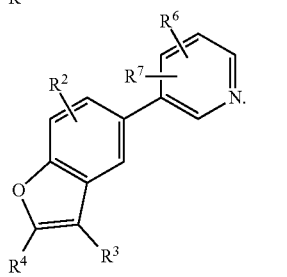
[B7] The composition according to any one of [B1] to [B5], wherein the compound represented by formula (I) is
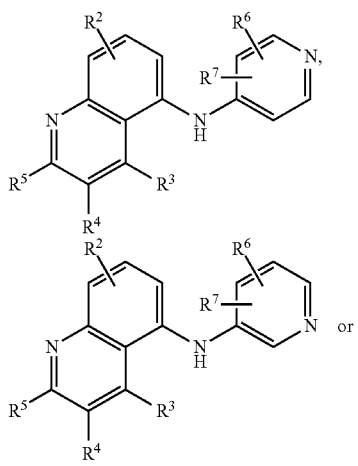
or
-continued
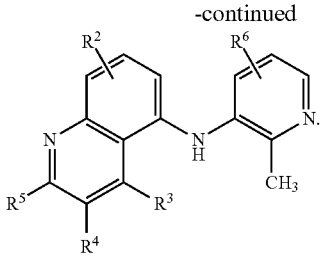
[B8] The composition according to any one of [B1] to [B5], wherein the compound represented by formula (I) is
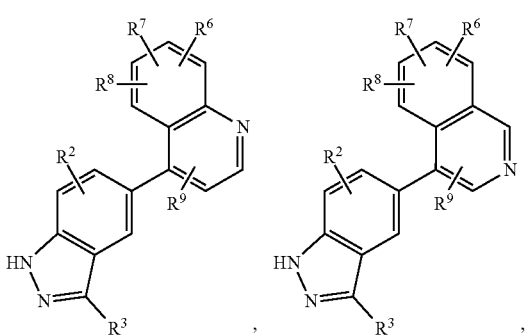
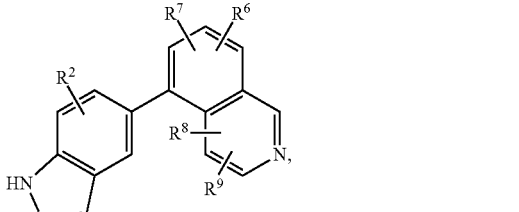
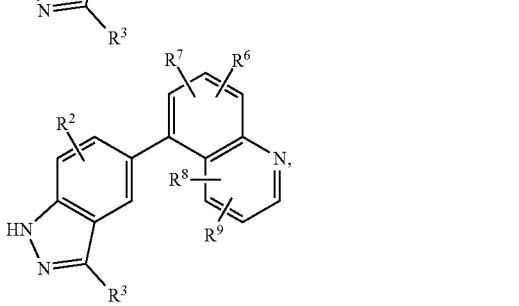
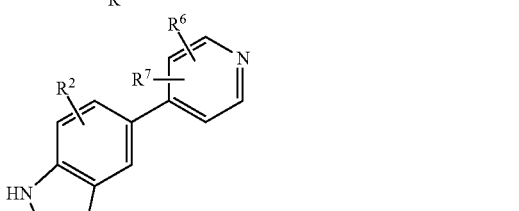
or
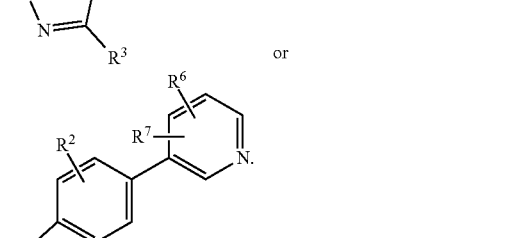

[B9] The composition according to any one of [B1] to [B8], which is a pharmaceutical composition.

[B10] The pharmaceutical composition according to [B9] for preventing, improving, inhibiting the development of, and/or treating a disease of the central nervous system and/or the peripheral nervous system, or for improving, inhibiting the development of, and/or treating a functional disorder of the central nervous system and/or the peripheral nervous system.

[B11] A method for preventing, improving, inhibiting the development of, and/or treating a disease of the central nervous system and/or the peripheral nervous system, or for improving, inhibiting the development of, and/or treating a functional disorder of the central nervous system and/or the peripheral nervous system, the method including administering the composition according to any one of [B1] to [B8] or the pharmaceutical composition according to [B9] or [B10] to a subject.

[B12] The method according to [B11], wherein the subject is a human or a non-human animal.

[B13] Use of the compound represented by formula (I) or a prodrug thereof, or a pharmaceutically acceptable salt thereof to prevent, improve, inhibit the development of, and/or treat a disease of the central nervous system and/or the peripheral nervous system, or to improve, inhibit the development of, and/or treat a functional disorder of the central nervous system and/or the peripheral nervous system.

[B14] Use of the compound represented by formula (I) or a prodrug thereof, or a pharmaceutically acceptable salt thereof to manufacture a pharmaceutical composition for preventing, improving, inhibiting the development of, and/or treating a disease of the central nervous system and/or the peripheral nervous system, or for improving, inhibiting the development of, and/or treating a functional disorder of the central nervous system and/or the peripheral nervous system.

[B15] A method for inducing neurogenesis, including administering the composition according to any one of [B1] to [B8] or the pharmaceutical composition according to [B9] or [B10] to a subject.

[B16] The method according to [B15], wherein the subject is a cell, a tissue, an organ, an individual, a human, or a non-human animal.

[B17] Use of the compound represented by formula (I) or a prodrug thereof, or a pharmaceutically acceptable salt thereof to activate neurogenesis.

[B18] Use of the compound represented by formula (I) or a prodrug thereof, or a pharmaceutically acceptable salt thereof to manufacture a pharmaceutical composition for activating neurogenesis.

Activation of Proliferation of Nerve Cells

In one or more embodiments, a compound having an ability to inhibit the phosphorylation activity of a protein kinase or a prodrug thereof, or a pharmaceutically acceptable salt thereof exhibits an effect of activating the proliferation of nerve cells. Accordingly, an aspect of the present disclosure relates to a composition for activating the proliferation of nerve cells, the composition containing, as an active ingredient, a compound having an ability to inhibit the phosphorylation activity of a protein kinase or a prodrug thereof, or a pharmaceutically acceptable salt thereof. It should be noted that the composition of this aspect may be a pharmaceutical composition.

In one or more embodiments, the term "nerve cells" as used in the present disclosure encompasses neural stem cells. As described above, the term "neural stem cells" as used in the present disclosure means cells that reside in the brain and spinal cord and produce precursor cells having an ability to differentiate into nerve cells or glia cells. In one or more embodiments, the term "proliferation of nerve cells" as used in the present disclosure means the proliferation of nerve cells or neural stem cells (also referred to as "neural (stem) cells" hereinafter). The term "proliferation of neural (stem) cells" as used in the present disclosure means the proliferation of neural (stem) cells in vitro, in vivo, or ex vivo in one or more embodiments, and means the proliferation of cultured neural stem cells in one or more embodiments. In one or more embodiments, the term "cultured neural stem cells" as used in the present disclosure means a cluster of neural stem cells that have been isolated from an organism and cultured. The term "activation of the proliferation of nerve cells" as used in the present disclosure means the activation of the proliferation of neural (stem) cells in one or more embodiments, and further means the promotion of the production of neural precursor cells in one or more other embodiments. The term "activation of the proliferation of nerve cells" as used in the present disclosure means the activation of the proliferation of neural (stem) cells in vitro, in vivo, or ex vivo in one or more embodiments, and means the proliferation of cultured neural stem cells in one or more other embodiments.

With the composition of this aspect, in one or more embodiments, the proliferation of cultured neural stem cells can be enhanced, and it is thus expected that the proliferation of neural stem cells resided in the brain and spinal cord in an organism is also promoted. Accordingly, in one or more embodiments, the present disclosure relates to a composition for activating cultured neural stem cells, the composition containing, as an active ingredient, the compound represented by formula (I) or a prodrug thereof, or a pharmaceutically acceptable salt thereof.

In one or more embodiments, the present disclosure relates to a method for proliferating neural (stem) cells, including culturing the neural (stem) cells in a culture medium containing the composition according to the present disclosure. In one or more embodiments, the present disclosure relates to a method for preparing neural (stem) cells, including culturing the neural (stem) cells in a culture medium containing the composition according to the present disclosure. In one or more embodiments, the present disclosure relates to use of the composition according to the present disclosure in the method for proliferating neural (stem) cells according to the present disclosure. In one or more embodiments, the present disclosure relates to use of the composition according to the present disclosure in the method for preparing neural (stem) cells according to the present disclosure.

That is, the present disclosure may relate to one or more embodiments below.

[C1] A composition for activating the proliferation of nerve cells, containing, as an active ingredient, a compound having an ability to inhibit the phosphorylation activity of a protein kinase or a prodrug thereof, or a pharmaceutically acceptable salt thereof.

[C2] A composition of activating the proliferation of neural (stem) cells, containing, as an active ingredient, a compound having an ability to inhibit the phosphorylation activity of a protein kinase or a prodrug thereof, or a pharmaceutically acceptable salt thereof.

[C3] The composition according to [C1] or [C2], wherein the compound is the compound represented by formula (I).

[C4] The composition according to any one of [C1] to [C3], which is a pharmaceutical composition.

[C5] A method for activating the proliferation of nerve cells, including culturing neural (stem) cells in a culture medium including a composition containing, as an active ingredient, a compound having an ability to inhibit the phosphorylation activity of a protein kinase or a prodrug thereof, or a pharmaceutically acceptable salt thereof.

[C6] A method for preparing neural (stem) cells, including culturing neural (stem) cells in a culture medium including a composition containing, as an active ingredient, a compound having an ability to inhibit the phosphorylation activity of a protein kinase or a prodrug thereof, or a pharmaceutically acceptable salt thereof.

[C7] Use of a composition containing, as an active ingredient, a compound having an ability to inhibit the phosphorylation activity of a protein kinase or a prodrug thereof, or a pharmaceutically acceptable salt thereof to activate the proliferation of nerve cells.

[C8] Use of a composition containing, as an active ingredient, a compound having an ability to inhibit the phosphorylation activity of a protein kinase or a prodrug thereof, or a pharmaceutically acceptable salt thereof to prepare neural (stem) cells.

[C9] Use of, as an active ingredient, a compound having an ability to inhibit the phosphorylation activity of a protein kinase or a prodrug thereof, or a pharmaceutically acceptable salt thereof to manufacture a composition for activating the proliferation of nerve cells.

[C10] Use of, as an active ingredient, a compound having an ability to inhibit the phosphorylation activity of a protein kinase or a prodrug thereof, or a pharmaceutically acceptable salt thereof to manufacture a composition for preparing neural (stem) cells.

The above-mentioned composition according to the present disclosure can be used as a pharmaceutical composition. In one or more embodiments, the "pharmaceutical composition" of the present disclosure can be formed in a medicinal substance form suitable for an administration form by applying a known pharmaceutical technique. An example of the administration form is oral administration using a medicinal substance form that is selected from, but is not limited to, a tablet, a capsule, granular medicine, powdered medicine, a pill, a troche, syrup, liquid medicine, and the like. Alternatively, an example thereof is parenteral administration using a medicinal substance form such as an injection, liquid medicine, an aerosol, a suppository, a plaster, a cataplasm, a lotion, a liniment, an ointment, or eyedrop medicine. An additive that is selected from, but is not limited to, a vehicle, a lubricant, a binder, a disintegrator, a stabilizer, a corrigent, a diluent, and the like may be used to manufacture these preparations using a known method. In one or more embodiments, the composition and the pharmaceutical composition according to the present disclosure may contain a pharmaceutically acceptable carrier in addition to the compound represented by formula (I) or a prodrug thereof, or a pharmaceutically acceptable salt thereof, which is an active ingredient. In one or more embodiments, examples of the pharmaceutically acceptable carrier include all solvents, dispersion mediums, coating agents, anti-bacterial agents, anti-fungal agents, isotonic agents, and absorption retardants for the active ingredients of a drug. Furthermore, in one or more embodiments, the composition and the pharmaceutical composition according to the present disclosure may contain at least one of a vehicle, a lubricant, a binder, a disintegrator, a stabilizer, a corrigent, and a diluent.

Examples of the vehicle include, but are not limited to, starch such as starch, potato starch, and corn starch, lactose, crystalline cellulose, and calcium hydrogen phosphate. Examples of the coating agent include, but are not limited to, ethylcellulose, hydroxypropylcellulose, hydroxypropylmethylcellulose, shellac, talc, carnauba wax, and paraffin. Examples of the binder include, but are not limited to, polyvinylpyrrolidone, macrogol, and compounds similar to those listed for the vehicle. Examples of the disintegrator include, but are not limited to, compounds similar to those listed for the vehicle, and chemically modified starch and cellulose such as sodium croscarmellose, sodium carboxymethyl starch, and cross-linked polyvinylpyrrolidone. Examples of the stabilizer include, but are not limited to, p-hydroxybenzoates such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid. Examples of the corrigent include, but are not limited to, sweetening agents, acidulants, and aromatic agents that are commonly used.

Ethanol, phenol, chlorocresol, purified water, or distilled water can be used as a solvent in the manufacturing of a liquid medicine, but there is no limitation thereto. A surfactant, an emulsifier, or the like can also be used as needed. Examples of the surfactant or emulsifier include, but are not limited to, polysorbate 80, polyoxyl 40 stearate, and lauromacrogol.

A method of using the composition and the pharmaceutical composition according to the present disclosure may vary depending on the symptoms, age, administration method, and the like. In such a usage method, the composition or the pharmaceutical composition can be intermittently or continuously administered orally, percutaneously, submucosally, subcutaneously, intramuscularly, intravascularly, intracerebrally, or intra-abdominally such that the concentration of the compound represented by formula (I), which is an active ingredient, in the body is any value within a range from 100 nM to 1 mM. In a non-limiting embodiment, when the composition or the pharmaceutical composition is orally administered to a subject (an adult in the case of a human), the minimum amount is 0.01 mg (preferably 0.1 mg) and the maximum amount is 2000 mg (preferably 500 mg, and more preferably 100 mg) per day in terms of the compound represented by formula (I), and the composition or the pharmaceutical composition is administered to the subject at once or over several times according to the symptom. In a non-limiting embodiment, when the composition or the pharmaceutical composition is intravenously administered to a subject (an adult in the case of a human), the minimum amount is 0.001 mg (preferably 0.01 mg) and the maximum amount is 500 mg (preferably 50 mg) per day, and the composition or the pharmaceutical composition is administered to the subject at once or over several times according to the symptom.

EXAMPLES

Hereinafter, the present disclosure will be more specifically described by way of experimental examples, but these experimental examples are merely exemplary, and the present disclosure is not limited to these experimental examples. It should be noted that all the references cited in the present disclosure are incorporated herein as parts of the present disclosure.

Compounds 1 to 15 below were prepared.
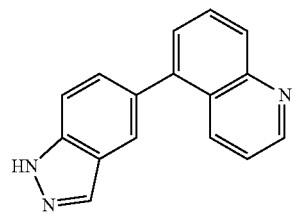
Compound 1
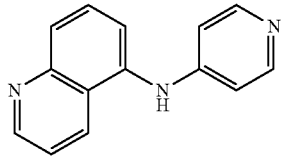
Compound 7
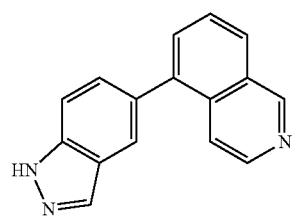
Compound 2
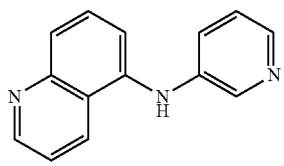
Compound 8
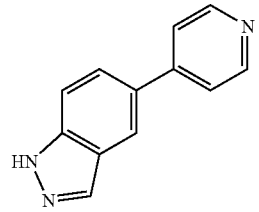
Compound 3
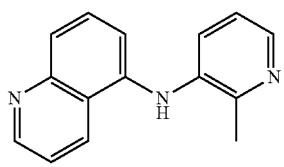
Compound 9
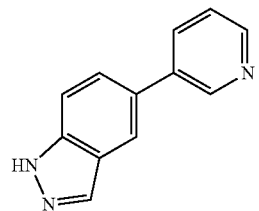
Compound 4
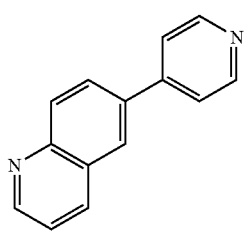
Compound 10
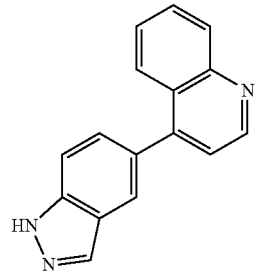
Compound 5
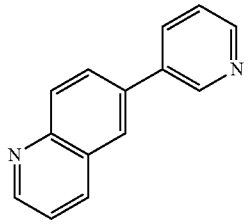
Compound 11
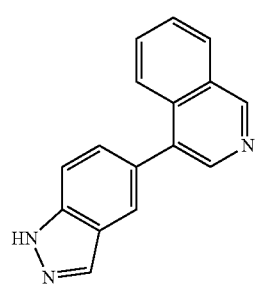
Compound 6
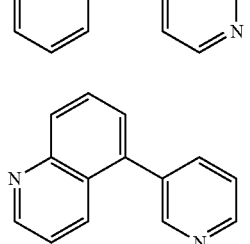
Compound 12
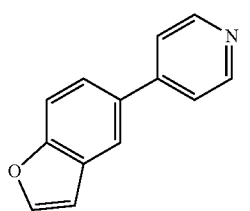
Compound 13
Compound 14

-continued

Compound 15

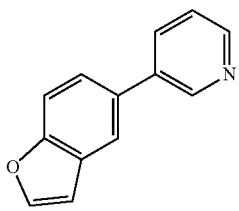

Methods of synthesizing Compounds 1, 2, 4, and 6, among Compounds 1 to 6, are shown below as representatives.

Method of Synthesizing Compound 1:

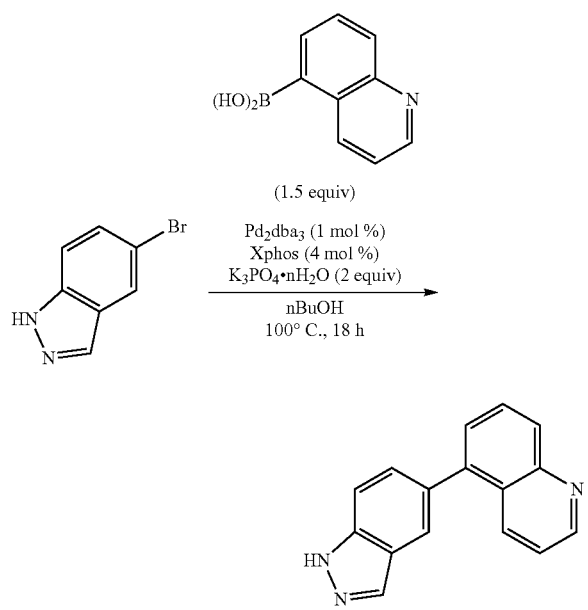

A solution of 5-bromoindazole (197 mg, 1.00 mmol, commercial product), 5-quinolineboronic acid (259 mg, 1.50 mmol, commercial product), dipalladium tris(dibenzylideneacetone) ($Pd_2dba_3$) (9.20 mg, 10.0 μmol, commercial product), 2-dicyclohexylphosphino-2',4',6'-triisopropylbiphenyl (Xphos) (19.1 mg, 40.1 μmol, commercial product), and tripotassium phosphate n-hydrate (425 mg, 2.00 mmol, commercial product) in 1-butanol (10 mL, commercial product) was heated and stirred at 100° C. for 18 hours in an argon atmosphere. After the solution was allowed to cool to room temperature, water (5 mL) was added thereto, and extraction was performed using ethyl acetate (5 mL×3). The organic layer was dried using sodium sulfate and filtered, and then the filtrate was concentrated under vacuum. The obtained residue was purified through medium-pressure column chromatography (Yamazen, AI-580 and ParallelFrac FR-360) (Yamazen Universal Columns Premium cartridge [silica] 40 g, chloroform/methanol=20/1), and then the obtained solid product was washed using dichloromethane. 5-(5-Quinolyl)indazole (Compound 1) (202 mg, 824 μmol, 82.4%) was thus obtained as a beige solid product.

TLC $R_f$=0.20 (dichloromethane/methanol=20/1); Mp 255° C. (decomp); $^1$H NMR (400 MHz, $CD_3OD$) δ 7.51-7.56 (m, 2H), 7.67 (dd, J=0.8, 6.8 Hz, 1H), 7.74 (d, J=8.4 Hz, 1H), 7.86-7.92 (m, 2H), 8.10 (d, J=8.4 Hz, 1H), 8.18 (d, J=0.8 Hz, 1H), 8.38 (d, J=8.0 Hz, 1H), 8.90 (dd, J=1.6, 4.4 Hz, 1H); $^{13}$C NMR (100 MHz, $CD_3OD$) δ 112.1, 123.4, 123.9, 125.5, 129.3, 129.4, 130.0, 131.1, 131.5, 134.0, 136.2, 137.5, 142.0, 143.4, 150.0, 151.9; IR (cm$^{-1}$) 746, 772, 802, 887, 918, 937, 1061, 1101, 1238, 1290, 1337, 1395, 1510, 1574, 1738, 2849, 2901, 2928, 3030, 3094.

Method of Synthesizing Compound 2:

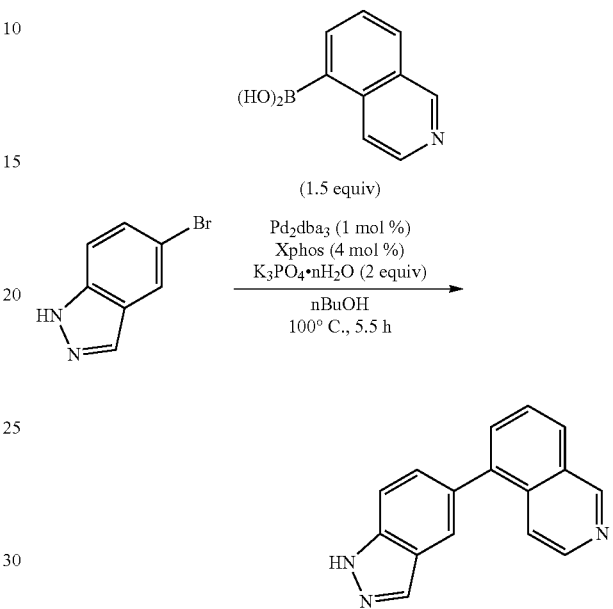

A solution of 5-bromoindazole (197 mg, 1.00 mmol, commercial product), 5-isoquinolineboronic acid (259 mg, 1.50 mmol, commercial product), dipalladium tris(dibenzylideneacetone) ($Pd_2dba_3$) (9.20 mg, 10.0 μmol, commercial product), 2-dicyclohexylphosphino-2',4',6'-triisopropylbiphenyl (Xphos) (19.1 mg, 40.1 μmol, commercial product), and tripotassium phosphate n-hydrate (425 mg, 2.00 mmol, commercial product) in 1-butanol (10 mL, commercial product) was heated and stirred at 100° C. for 5.5 hours in an argon atmosphere. After the solution was allowed to cool to room temperature, water (5 mL) was added thereto, and extraction was performed using ethyl acetate (5 mL×3). The organic layer was dried using sodium sulfate and filtered, and then the filtrate was concentrated under vacuum. The obtained residue was purified through medium-pressure column chromatography (Yamazen, AI-580 and ParallelFrac FR-360) (Yamazen Universal Columns Premium cartridge [silica] 40 g, chloroform/methanol=20/1), and 5-(5-isoquinolyl)indazole (Compound 2) (182 mg, 742 μmol, 74.2%) was thus obtained as a colorless solid product.

TLC $R_f$=0.20 (dichloromethane/methanol=20/1); Mp 250° C. (decomp.); $^1$H NMR (400 MHz, $CD_3OD$) δ 7.57 (dd, J=1.6, 8.8 Hz, 1H), 7.75 (d, J=8.8 Hz, 1H), 7.79-7.88 (m, 3H), 7.94 (dd, J=0.8, 1.6 Hz, 1H), 8.17-8.20 (m, 2H), 8.44 (d, J=6.4 Hz, 1H), 9.35 (d, J=0.8 Hz, 1H); $^{13}$C NMR (100 MHz, $CD_3OD$) δ 112.2, 121.3, 123.8, 125.5, 129.3, 129.5, 131.0, 131.5, 133.7, 134.1, 136.2, 136.9, 141.8, 142.0, 144.0, 154.5; IR (cm$^{-1}$) 650, 712, 754, 768, 779, 812, 835, 895, 943, 986, 1034, 1161, 1292, 1342, 1379, 1489, 1585, 1614, 2770, 2851, 2901, 3030, 3117.

Method of Synthesizing Compound 4:

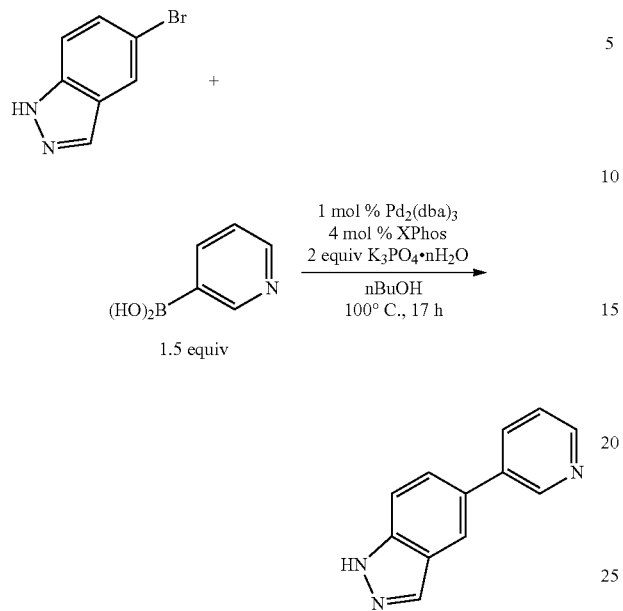

Method of Synthesizing Compound 6:

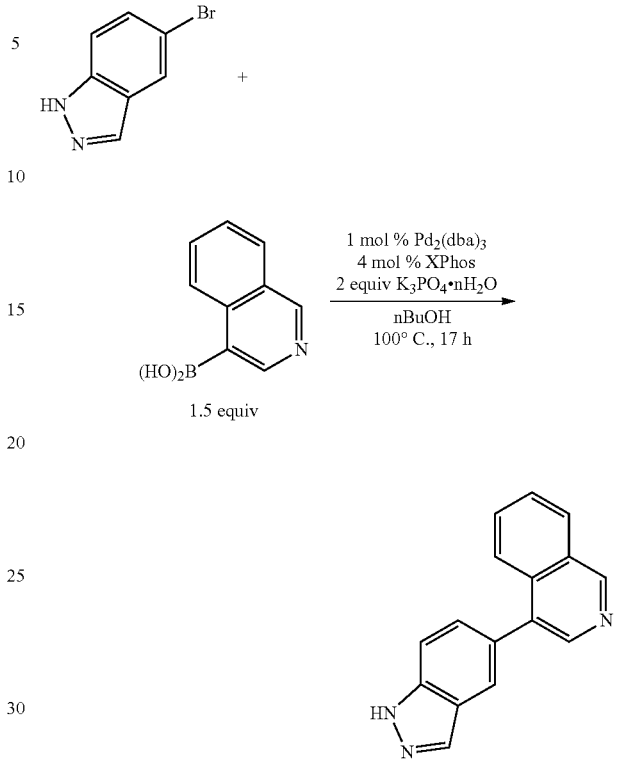

In an argon atmosphere, n-butanol (50 mL, nacalai, 06015-95) was added to dipalladium tris(dibenzylideneacetone) (Pd$_2$(dba)$_3$) (56.7 mg, 61.9 μmol, Aldrich, 328774), 2-dicydohexylphosphino-2',4',6'-triisopropylbiphenyl (XPhos) (118 mg, 0.247 mmol, Aldrich, 638064), potassium phosphate n-hydrate (2.63 g, <12.4 mmol, nacalai, 28730-35), 5-bromoindazole (1.22 g, 6.19 mmol, TCI, B3785), and 3-pyridylboronic acid (1.14 g, 9.27 mmol, WAKO, 328-59843), and the resultant suspension was heated and stirred at 100° C. (oil bath temperature) for 17 hours. The mixture was allowed to cool to room temperature and then filtered using a Gooch funnel into which a small amount of silica gel had been filled, and vacuum concentration was performed. The obtained light yellow solid product was separated through filtration using a Kiriyama funnel. The solid product on the funnel was washed using distilled water and ethyl acetate, and then dried under reduced pressure. Compound 4 (272 mg, 1.39 mmol, 22.5%) was thus obtained as a milky white solid product. Furthermore, the filtrate was subjected to extraction using ethyl acetate. The obtained organic layer was dried using anhydrous sodium sulfate and filtered, and then vacuum concentration was performed. The obtained milky white solid product was separated through filtration using a Kiriyama funnel. The solid product on the funnel was washed (hexane/ethyl acetate=5/1), and then purification using recrystallization was performed (ethyl acetate/methanol=10/1). Compound 4 (211 mg, 1.08 mmol, 17.5%) was thus obtained as a milky white solid product (40% in total).

TLC R$_f$=0.25 (CH$_2$Cl$_2$/MeOH=20/1); $^1$H NMR (CD$_3$OD, 400 MHz) δ 8.88 (dd, J=2.4, 0.8 Hz, 1H), 8.53 (dd, J=4.8, 1.6 Hz, 1H), 8.19-8.16 (m, 2H), 8.11 (dd, J=2.4, 1.6 Hz, 1H), 7.74 (dd, J=5.2, 1.6 Hz, 1H), 7.70 (d, J=5.2 Hz, 1H), 7.56 (ddd, J=8.0, 4.8, 0.8 Hz, 1H) (The signal for NH of indazole was not observed); $^{13}$C NMR (CD$_3$OD, 400 MHz) δ 149.4, 149.1, 142.2, 140.0, 137.5, 136.4, 132.4, 128.3, 126.3, 125.9, 121.3, 112.9.

In an argon atmosphere, n-butanol (40 mL, nacalai, 06015-95) was added to dipalladium tris(dibenzylideneacetone) (Pd$_2$(dba)$_3$) (39.8 mg, 43.5 μmol, Aldrich, 328774), 2-dicydohexylphosphino-2',4',6'-triisopropylbiphenyl (XPhos) (83.0 mg, 0.174 mmol, Aldrich, 638064), potassium phosphate n-hydrate (1.85 g, <8.70 mmol, nacalai, 28730-35), 5-bromoindazole (857 g, 4.35 mmol, TCI, B3785), and 4-isoquinolineboronic acid (1.13 g, 6.53 mmol, Aldrich, 707929), and the resultant suspension was heated and stirred at 100° C. (oil bath temperature) for 18 hours. After the suspension was allowed to cool to room temperature, distilled water (5 mL) was added thereto, and the mixture was subjected to extraction using ethyl acetate. The obtained organic layer was filtered using a small amount of silica gel and dried using anhydrous sodium sulfate. After filtration, vacuum concentration was performed. The residue was purified through medium-pressure column chromatography (YAMAZEN, Smart Flash Al-580S, chloroform/methanol=20/1), and Compound 6 (972 mg, 3.96 mmol, 91.1%) was thus obtained as a milky white solid product.

TLC R$_f$=0.20 (CH$_2$Cl$_2$/MeOH=20/1); $^1$H NMR (CDCl$_3$, 400 MHz) δ 10.46 (br s, 1H), 9.29 (s, 1H), 8.55 (s, 1H), 8.19 (s, 1H), 8.07 (d, J=8.0 Hz, 1H), 7.92 (d, J=6.8 Hz, 1H), 7.91 (s, 1H), 7.68-7.64 (m, 3H), 7.56 (d, J=8.0 Hz, 1H); $^{13}$C NMR (CDCl$_3$, 400 MHz) δ 152.3, 143.5, 140.1, 135.7, 134.9, 133.7, 131.0, 130.3, 129.7, 128.8, 128.3, 127.6, 125.2, 124.0, 122.6, 110.1.

A method of synthesizing Compound 8, among Compounds 7 to 9, is shown below as a representative.

Method of Synthesizing Compound 8

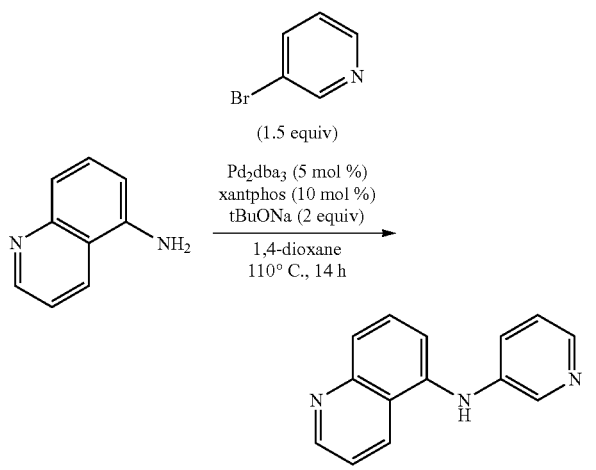

A solution of 5-aminoquinoline (144 mg, 999 μmol, commercial product), 3-bromopyridine (150 μL, 1.54 mmol, commercial product), dipalladium tris(dibenzylideneacetone) (Pd$_2$dba$_3$) (45.8 mg, 50.0 μmol, commercial product), 4,5-bis(diphenylphosphino)-9,9-dimethylxanthene (xantphos) (57.9 mg, 100 μmol, commercial product), and tert-butoxy sodium (192 mg, 2.00 mmol, commercial product) in 1,4-dioxane (10 mL, commercial product) was heated and stirred at 110° C. for 14 hours in an argon atmosphere. After the solution was allowed to cool to room temperature, water (5 mL) was added thereto, and extraction was performed using ethyl acetate (5 mL×3). The organic layer was dried using sodium sulfate and filtered, and then the filtrate was concentrated under vacuum. The obtained residue was roughly purified through medium-pressure column chromatography (Yamazen, W-Prep 2XY A-type) (Biotage ZIP (trademark) sphere cartridge [silica] 30 g, dichloromethane/methanol=20/1→5/1), and then the obtained solid product was washed using hexane/dichloromethane=30/1. 5-(3-Pyridylamino)quinoline (Compound 8) (120 mg, 542 μmol, 54.3%) was thus obtained as a light yellow solid product.

TLC $R_f$=0.30 (dichloromethane/methanol=20/1); Mp 180° C. (decomp.); $^1$H NMR (400 MHz, CDCl$_3$) δ 6.08 (br s, 1H), 7.13-7.22 (m, 2H), 7.38-7.42 (m, 2H), 7.66 (dd, J=8.8, 8.8 Hz, 1H), 7.91 (d, J=8.8 Hz, 1H), 8.18 (dd, J=1.6, 4.4 Hz, 1H), 8.33-8.37 (m, 2H), 8.95 (dd, J=1.6, 4.4 Hz, 1H); $^{13}$C NMR (100 MHz, CDCl$_3$) δ 117.5, 120.8, 123.1, 123.3, 123.8, 125.6, 129.6, 130.6, 137.7, 139.6, 141.2, 142.0, 149.3, 150.7; IR (cm$^{-1}$) 652, 710, 762, 783, 814, 966, 1018, 1063, 1240, 1294, 1317, 1395, 1470, 1485, 1537, 1570, 3005, 3044, 3109, 3175.

Methods of synthesizing Compounds 10 and 12, among Compounds 10 to 13, are shown below as representatives.

Method of Synthesizing Compound 10:

+

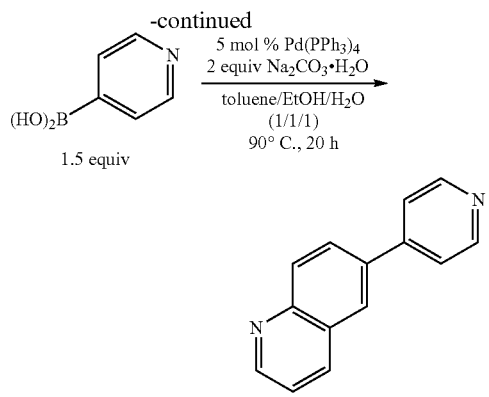

A mixed solution of palladium tetrakistriphenylphosphine (Pd(PPh$_3$)$_4$) (57.8 mg, 50.0 μmol, Aldrich, 216666), sodium carbonate monohydrate (248 mg, 2.00 mmol, WAKO, 193-04925), 6-bromoquinoline (208 mg, 1.00 mmol, WAKO, 325-53253), 4-pyridylboronic acid (184 mg, 1.50 mmol, WAKO, 325-59853) in distilled toluene (3 mL), ethanol (3 mL, nacalai, 14719-35), and distilled water (3 mL) was heated and stirred at 90° C. (oil bath temperature) for 20 hours in an argon atmosphere. After the solution was allowed to cool to room temperature, distilled water was added thereto, and the mixture was subjected to extraction using ethyl acetate. The obtained organic layer was dried using anhydrous sodium sulfate and filtered, and then vacuum concentration was performed. The residue was purified through medium-pressure column chromatography (YAMAZEN, SmartFlash Al-580S, chloroform/methanol=99/1), and Compound 10 (168 mg, 0.813 mmol, 81.3%) was thus obtained as a milky white solid product.

TLC $R_f$=0.20 (only ethyl acetate), $R_f$=0.25 (CH$_2$Cl$_2$/MeOH=20/1); $^1$H NMR (CDCl$_3$, 400 MHz) δ 8.98 (dd, J=4.4, 1.6 Hz, 1H), 8.73 (dd, J=4.4, 2.0 Hz, 2H), 8.27-8.22 (m, 2H), 8.09 (d, J=2.0 Hz, 1H), 8.00 (dd, J=8.8, 2.0 Hz, 1H), 7.64 (dd, J=4.4, 2.0 Hz, 2H), 7.48 (dd, J=8.0, 4.0 Hz, 1H); $^{13}$C NMR (CDCl$_3$, 400 MHz) δ 151.6, 150.8 (2C), 148.7, 147.8, 136.8, 136.6, 130.9, 128.7, 128.6, 126.6, 122.2 (3C).

Method of Synthesizing Compound 12:

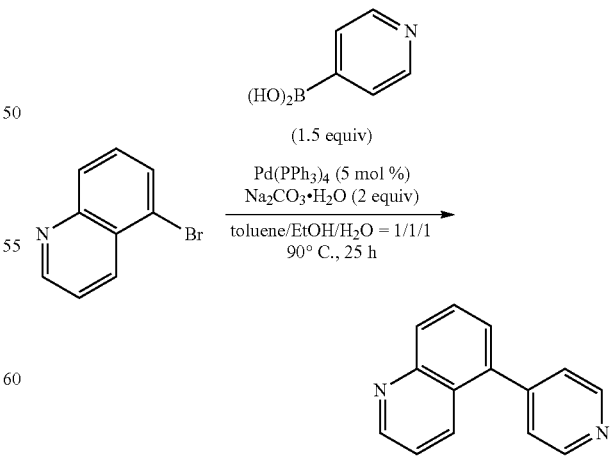

A mixed solution of 5-bromoquinoline (84.2 mg, 405 μmol, commercial product), 4-pyridylboronic acid (73.8 mg, 600 μmol, commercial product), palladium tetrakis (triphenylphosphine) (Pd(PPh$_3$)$_4$) (23.1 mg, 20.0 μmol, commercial product), sodium carbonate monohydrate (99.2 mg, 800 μmol, commercial product) in toluene (1.3 mL, commercial product), ethanol (1.3 mL, commercial product), and purified water (1.3 mL) was heated and stirred at 90° C. for 25 hours in an argon atmosphere. After the solution was allowed to cool to room temperature, water (2 mL) was added thereto, and extraction using ethyl acetate (2 mL×3) was performed. The organic layer was dried using sodium sulfate and filtered, and then the filtrate was concentrated under vacuum. The obtained residue was purified through medium-pressure column chromatography (Yamazen, W-Prep 2XY A-type) (Biotage ZIP (trademark) sphere cartridge [silica] 30 g, ethyl acetate 100%→dichloromethane/methanol=95/5), and (4-pyridyl)quinoline (Compound 12) (77.7 mg, 377 μmol, 93.0%) was thus obtained as a yellow solid product.

TLC R$_f$=0.35 (dichloromethane/methanol=20/1); Mp 113° C.; $^1$H NMR (400 MHz, CDCl$_3$) δ 7.39-7.43 (m, 3H), 7.52 (dd, J=1.2, 7.2 Hz, 1H), 7.80 (dd, J=7.2, 8.8Hz, 1H), 8.17-8.22 (m, 2H), 8.75-8.78 (AA'BB', 2H), 8.98 (dd, J=1.6, 4.0 Hz, 1H); $^{13}$C NMR (100 MHz, CDCl$_3$) δ 121.6, 124.9 (2C), 125.9, 127.3, 128.9, 130.3, 133.4, 137.5, 147.2, 148.5, 150.0 (2C), 150.7; IR (cm$^{-1}$) 650, 696, 743, 750, 797, 839, 962, 989, 1111, 1229, 1304, 1391, 1418, 1495, 1543, 1570, 1589, 3026.

A method of synthesizing Compound 14, out of Compounds 14 and 15, is shown below as a representative.

Method of Synthesizing Compound 14:

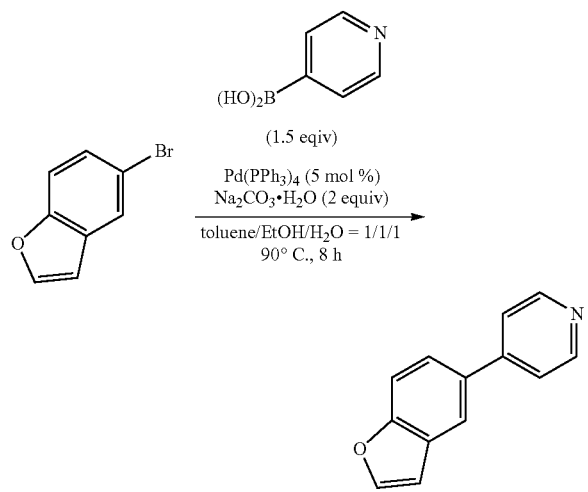

A mixed solution of 5-bromobenzofuran(79.6 mg, 404 μmol, commercial product), 4-pyridylboronic acid (73.8 mg, 600 μmol, commercial product), palladium tetrakis(triphenylphosphine) (Pd(PPh$_3$)$_4$) (23.1 mg, 20.0 μmol, commercial product), and sodium carbonate monohydrate (99.2 mg, 800 μmol, commercial product) in toluene (1.3 mL, commercial product), ethanol (1.3 mL, commercial product), and purified water (1.3 mL) was heated and stirred at 90° C. for 8 hours in an argon atmosphere. After the solution was allowed to cool to room temperature, water (2 mL) was added thereto, and extraction using ethyl acetate (2 mL×3) was performed. The organic layer was dried using sodium sulfate and filtered, and then the filtrate was concentrated under vacuum. The obtained residue was purified through medium-pressure column chromatography (Yamazen, W-Prep 2XY A-type) (Biotage ZIP (trademark) sphere cartridge [silica] 45 g, dichloromethane/methanol=10/1), and then recrystallization was performed. 5-(4-Pyridyl)benzofuran (Compound 14) (56.8 mg, 289 μmol, 71.6%) was thus obtained as a colorless solid product.

TLC R$_f$=0.50 (dichloromethane/methanol=10/1); Mp 96° C.; $^1$H NMR (400 MHz, CDCl$_3$) δ 6.84 (dd, J=0.8, 2.0 Hz, 1H), 7.52-7.54 (AA'BB', 2H), 7.54-7.62 (m, 2H), 7.68 (d, J=2.0 Hz, 1H), 7.86 (dd, J=0.4, 1.6 Hz, 1H), 8.64-8.66 (AA'BB', 2H); $^{13}$C NMR (100 MHz, CDCl$_3$) δ 106.8, 112.0, 119.9, 121.9 (2C), 123.6, 128.2, 133.3, 146.1, 148.8, 150.2 (2C), 155.4; IR (cm$^{-1}$) 746, 775, 806, 874, 1018, 1109, 1219, 1265, 1414, 1460, 1537, 1595, 1728, 2853, 2924, 3036, 3094.

Experimental Example 1: Evaluation of Inhibitory Activity of Compounds 4 and 10 Against DYRK1A Kinase The inhibitory activity of Compounds 4 and 10 against DYRK1A was examined through in-vitro kinase assay (in-vitro kinase analysis).

The inhibitory activity of Compounds 4 and 10 against DYRK1A was examined in the presence of DYRK1A protein using a DYRK peptide as a substrate under the condition of 10 μM ATP. FIG. 1 shows the results.

As shown in FIG. 1, in the in-vitro kinase analysis against DYRK1A, Compounds 4 and 10 had an IC$_{50}$ of 55.65 nM and an IC$_{50}$ of 59.72 nM, respectively, and exhibited high inhibitory activity against DYRK1A.

The same experiment was also performed using Compound 6. Compound 6 had inhibitory activity against DYRK1A, which was lower than that of Compounds 4 and 10.

Figure 2:
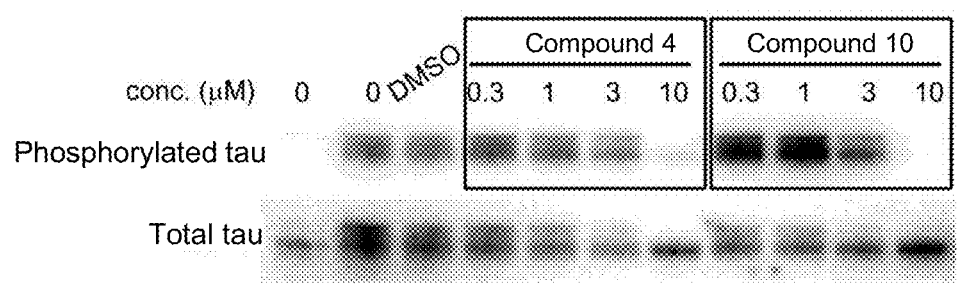
FIG. 2 is an example of the result of Western blotting showing the inhibitory activity of Compounds 4 and 10 against a kinase in cells.

Experimental Example 2: Evaluation of Inhibitory Activity of Compounds 4 and 10 Against Kinase in Cell Tau protein, which is a substrate of a target kinase, was overexpressed in cells in the presence of Compound 4 or 10 at a concentration of 0.3 μM, 1 μM, 3 μM, or 10 μM, and the inhibitory activity of Compounds 4 and 10 was examined using the phosphorylation of the tau protein as an index. FIG. 2 shows the results.

FIG. 2 is an example of the result of Western blotting analysis of cultured cells in which the expression of both tau protein and DYRK1A protein was induced in the presence of Compound 4 or 10 at a concentration of 0.3 μM, 1 μM, 3 μM, or 10 μM, using an antibody that specifically recognizes the phosphorylated threonine residue at 212-position of tau protein was used to analyze.

As shown in FIG. 2, Compounds 4 and 10 exhibited a high inhibitory effect against the phosphorylation of tau protein. The same evaluation was also performed on Compound 6. The inhibitory activity of Compound 6 showed the same tendency as Compounds 4 and 10.

Experimental Example 3: Proliferation Promoting Effect of Compounds 4 and 10 on Cultured Neural Stem Cells Mouse neural stem cells were treated with Compound 4 or 10, and then neural stem cell proliferating activity was examined using, as an index, uptake of 5-bromo-2'-deoxyuridine (BrdU), which is a nucleoside analog to be used as a proliferation index.

Figure 3:
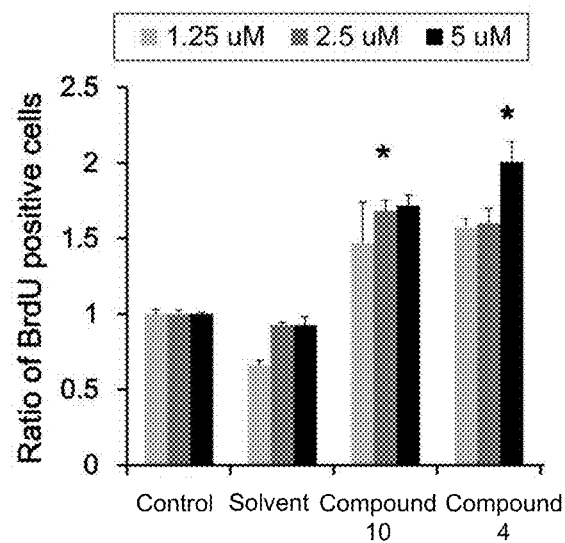
FIG. 3 is a graph showing an example of the result of array scanning of the ratio of BrdU-positive cells in neural stem cells of mice treated with Compound 4 or 10, as relative values by using the ratio of BrdU-positive cells of the control sample is defined as 1.

Specifically, isolated neural stem cells were cultured in the presence of BrdU and Compound 4 or 10 at a concentration of 1.25 µM, 2.5 µM, or 5 µM, so that proliferating cells were labeled. After the cells were fixed, BrdU was detected by an anti-BrdU antibody, and the ratio of proliferating cells that had incorporated the BrdU was quantitatively analyzed using Arrayscan (Thermo Scientific). FIG. 3 shows the results. In FIG. 3, "Control" indicates the results from adding no compounds, and "Solvent" indicates dimethyl sulfoxide (DMSO).

FIG. 3 is a graph showing the ratio of BrdU-positive cells as relative values determined based on the results from the control sample taken as 1. As shown in FIG. 3, the addition of Compounds 4 and 10 increased the amount of incorporation of BrdU, which is a proliferation index, into the neural stem cells. Accordingly, Compounds 4 and 10 can promote the proliferation of cultured neural stem cells.

The same evaluation was also performed on Compound 6. It could be confirmed that Compound 6 at concentrations of 2.5 µM and 5 µM promoted the proliferation of cultured neural stem cells as in the cases of Compounds 4 and 10.

Experimental Example 4: Expression of Cyclin D1 in Cultured Neural Stem Cells Treated with Compounds 4, 6, and 10

Figure 4:
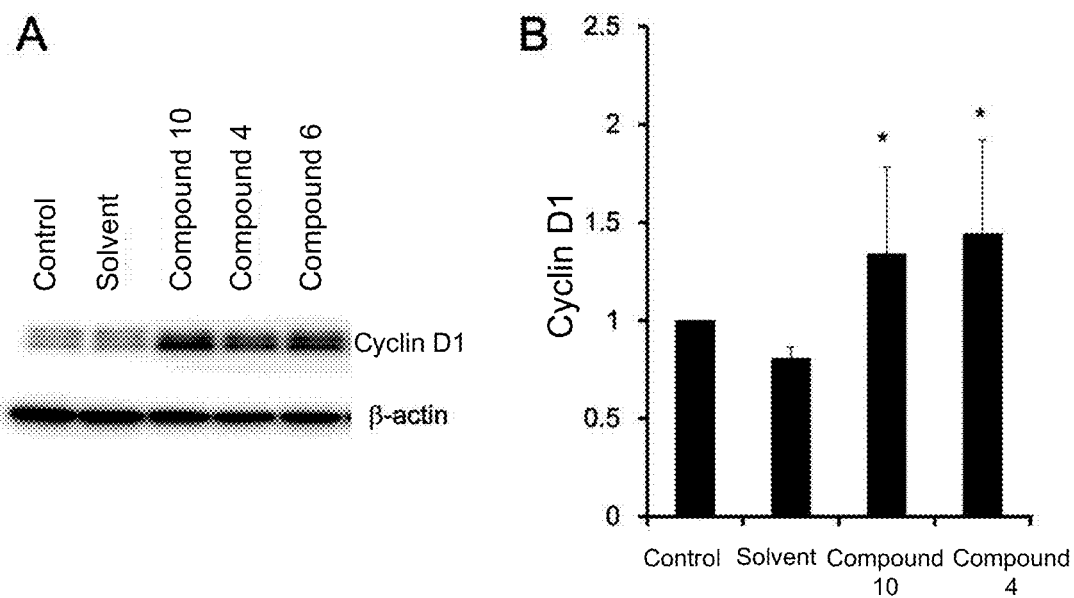
FIG. 4A is an example of the result of Western blotting.
FIG. 4B is a graph showing the expression levels of cyclin D1 as relative values by using the expression levels of the control sample is defined as 1.

Mouse neural stem cells were treated with Compound 4, 6, or 10, and the expression level of cyclin D1, which positively controls cell proliferation, was examined through Western blotting. FIGS. 4A and 4B show the results. In FIGS. 4A and 4B, "Control" indicates the results from adding no compounds, and "Solvent" indicates dimethyl sulfoxide (DMSO).

FIG. 4A shows an example of the result of Western blotting, and FIG. 4B is a graph showing the expression level of cyclin D1 as relative values determined based on the results from the control sample taken as 1.

As shown in FIGS. 4A and 4B, the expression level of cyclin D1 of the cells treated with Compound 4, 6, or 10 was significantly high. Accordingly, Compounds 4, 6, and 10 activate the proliferation of cultured neural stem cells.

Figure 5:
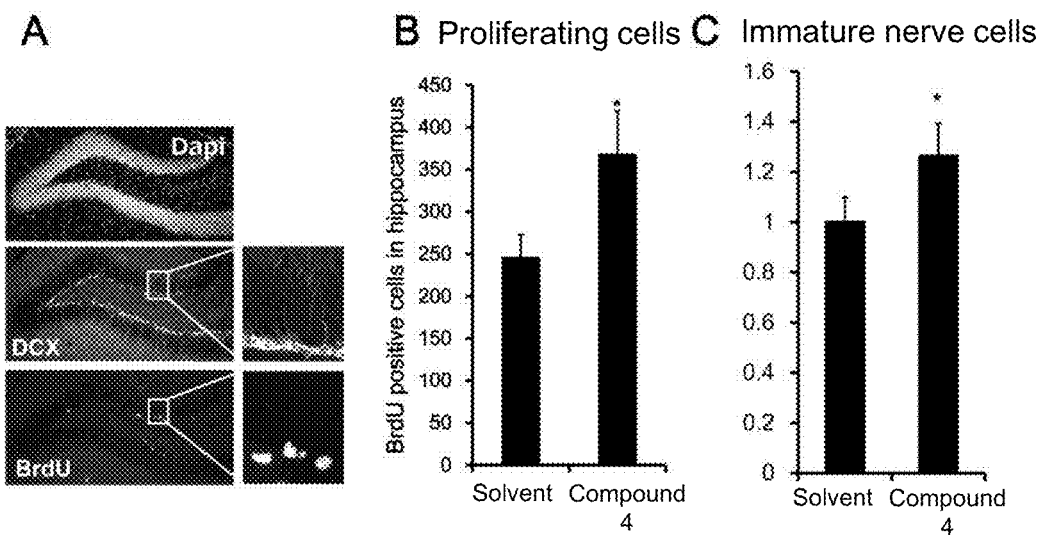
FIG. 5A is a representative images of thin sections of the dentate gyrus of the hippocampus, and the image of Dapi staining, the image of doublecortin (DCX) staining, and the image of BrdU staining are shown in the order from top to bottom.
FIG. 5B is a graph showing the number of BrdU-positive cells in the dentate gyrus of the hippocampus.
FIG. 5C is a graph showing the number of immature nerve cells in the dentate gyrus of the hippocampus as a relative value by using the number of immature nerve cells of the solvent sample is defined as 1.

Experimental Example 5: The Effect of Compound 4 Enhancing Neurogenesis in the Dentate Gyrus of the Hippocampus After 10-day long administration of Compound 4 to a rodent, BrdU was administered thereto, and the number of proliferating cells was quantitatively evaluated. FIGS. 5A to 5C shows the results. In FIGS. 5B and 5C, "Solvent" indicates the results from adding no compound.

FIG. 5A is a representative images of thin sections of the dentate gyrus of the hippocampus, and the image of Dapi staining (nucleus staining), the image of doublecortin (DCX) staining, and the image of BrdU staining are shown in the order from top to bottom. FIG. 5B is an example of a graph showing the number of BrdU-positive cells in the dentate gyrus of the hippocampus. FIG. 5C is an example of a graph showing the number of immature neurons in the dentate gyrus of the hippocampus as a relative value determined based on the result from the solvent sample taken as 1.

As shown in FIGS. 5B and 5C, the numbers of proliferating cells and immature neurons were significantly larger in the compound administered group than in the solvent administered group. Accordingly, Compound 4 acts on neural stem cells present in the dentate gyrus of the hippocampus of an animal individual (rodent) and significantly enhance neurogenesis in the dentate gyrus of the hippocampus.

Figure 6:
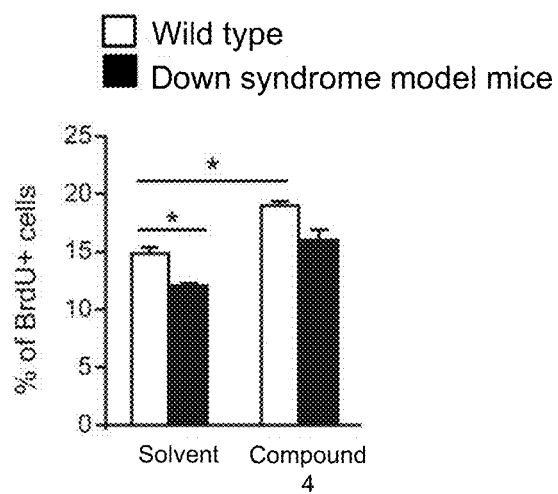
FIG. 6 is a graph showing the ratios of BrdU-positive cells in neural stem cells isolated from wild-type mice and Down syndrome model mice to which Compound 4 was administered.

Experimental Example 6: Effect of Compound 4 on Neural Stem Cells Derived from Down Syndrome Model Mouse Neural stem cells were prepared from wild-type mice and Down syndrome model mice (Ts1Cje: the same applies hereinafter), and the effect of Compound 4 on the proliferation of neural stem cells isolated Down syndrome model mice was examined. FIG. 6 shows the results. In FIG. 6, "Solvent" indicates the results from no adding compound.

FIG. 6 is an example of a graph showing the ratios of BrdU-positive cells in neural stem cells isolated wild-type mice and Down syndrome model mice to which Compound 4 was administered. As shown in FIG. 6, treatment with Compound 4 compensated for the reduced proliferation in the neural stem cells isolated Down syndrome model mice.

Figure 7:
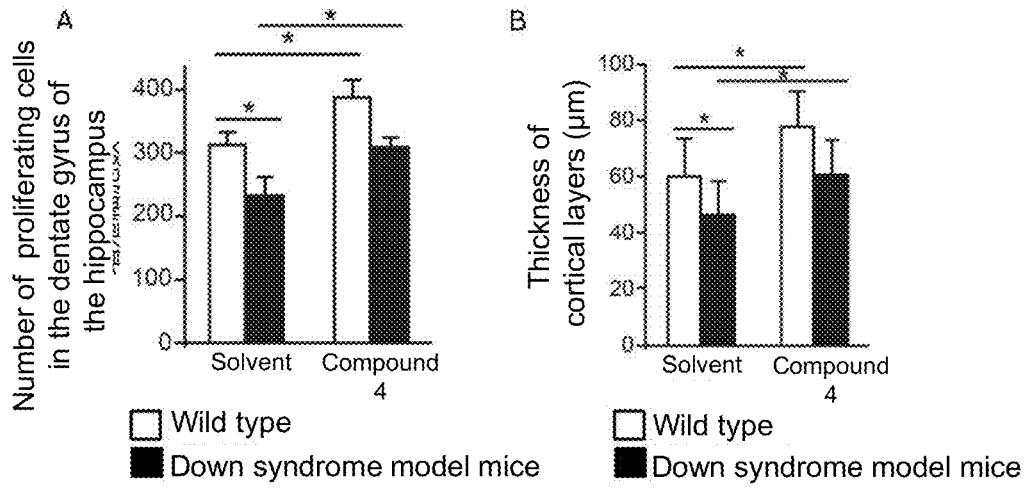
FIG. 7A is a graph showing examples of the number of proliferating cells in a dentate gyrus of the hippocampus.
FIG. 7B is a graph showing examples of the thickness of cortical layers.

Experimental Example 7: Effect of Compound 4 on Neurogenesis in Down Syndrome Model Mouse First, a solvent or Compound 4 was administered to 8-week old wild-type mice and 8-week old Down syndrome model mice, and the effect on neurogenesis in the dentate gyrus of the hippocampus was examined. FIG. 7A shows the results.

Moreover, Compound 4 was orally administered to pregnant mice carrying Down syndrome model mice from the tenth day to fifteenth day of fetal life, and the thickness of the cerebral cortex was measured at the fifteenth day of fetal life. FIG. 7B shows the results. In FIGS. 7A and 7B, "Solvent" indicates the results from adding no compound.

FIG. 7A is a graph showing examples of the number of proliferating cells in a dentate gyrus of the hippocampus, and FIG. 7B is an example of a graph showing examples of the thickness of cortical layers. As shown in FIG. 7A, the administration with Compound 4 compensated for the reduced neurogenesis in Down syndrome model mice. Moreover, as shown in FIG. 7B, the administration with Compound 4 to pregnant mice carrying Down syndrome model mouse compensated for the cerebral cortex with a reduced thickness in the Down syndrome model mice (fetus).

Figure 8:
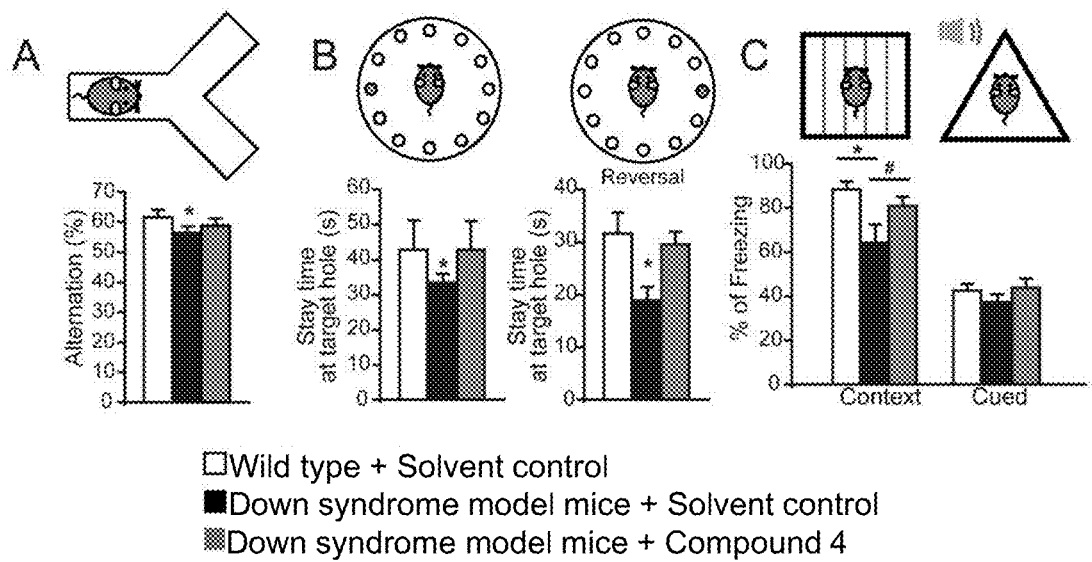
FIGS. 8A, 8B and 8C show graphs showing examples of the results of three types of tests analysis of the learning and memory of wild-type mice and Down syndrome model mice to which Compound 4 or a solvent has been administered.

Experimental Example 8: Effect of Prenatal Administration of Compound 4 to Down Syndrome Model Compound 4 (10 mg/kg) or a solvent was orally administered to pregnant mice carrying Down syndrome model mice once a day from the tenth day of fetal life until birth. After birth, at the age of 8 weeks, three types of tests (A. Y maze test for spontaneous alteration behavior, B. Barnes maze test for spatial memory, and C. fear conditioning test) were performed successively. FIGS. 8A to 8C show the results. In FIGS. 8A to 8C, "Solvent" indicates the results from adding no compound.

FIGS. 8A to 8C show graphs showing examples of the results of the above-mentioned three types of tests. FIG. 8A shows examples of the results of the Y maze test for spontaneous exploration behavior, FIG. 8B shows examples of the results of the Barnes maze test for spatial memory, and FIG. 8C shows examples of the results of the fear conditioning test. In FIGS. 8A to 8C, the white bars in the graphs indicate the results from wild-type mice to which a solvent was administered, the black bars in the graphs indicate the results from Down syndrome model mice to which a solvent was administered, and the gray bars in the graphs indicate the results from Down syndrome model mice to which Compound 4 was administered. As shown in FIGS. 8A to 8C, the cognitive function of the Down syndrome model mice (black) to which a solvent was administered was impaired compared with the wild-type mice (white), but the administration (prenatal administration) of Compound 4 to pregnant mice with a Down syndrome model mice in the womb improved the cognition function of the Down syndrome model mice (gray) that was born therefrom.

Experimental Example 9: Effect of Compound 4 on Facial Nerve Palsy Model Mouse

Figure 9:
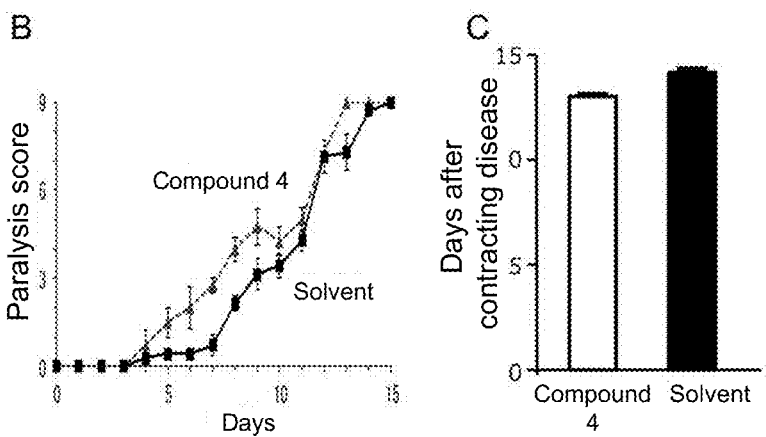
FIG. 9A shows paralysis scores used for the evaluation.
FIGS. 9B and 9C show the paralysis scores over the days of administration.

A facial nerve trunk (3 mm) of a rodent (ICR mouse; 6 to 8 weeks old) was extracted and compressed using a Mosquito forceps with a width of 1 mm for 30 seconds. Facial nerve palsy model mice were thus produced. Compound 4 (10 mg/kg) was administered every day from an hour before the operation (day 0), and paralysis scores relating to nictitation ("no eye-opening" to "cured"), a nose ("extended" to "cured"), and whiskers ("no movement" to "cured") were evaluated according to four levels. FIGS. 9A to 9C shows the results. In FIG. 9A, "Solvent" indicates the results from adding no compound.

FIG. 9A shows paralysis scores used for the evaluation. FIGS. 9B and 9C show the paralysis scores over the days of administration. As shown in FIGS. 9B and 9C, it was observed that the administration of Compound 4 tended to promote recovery.

Experimental Example 10: Effect of Compound 4 on Damaged Vertebra Model

Figure 10:
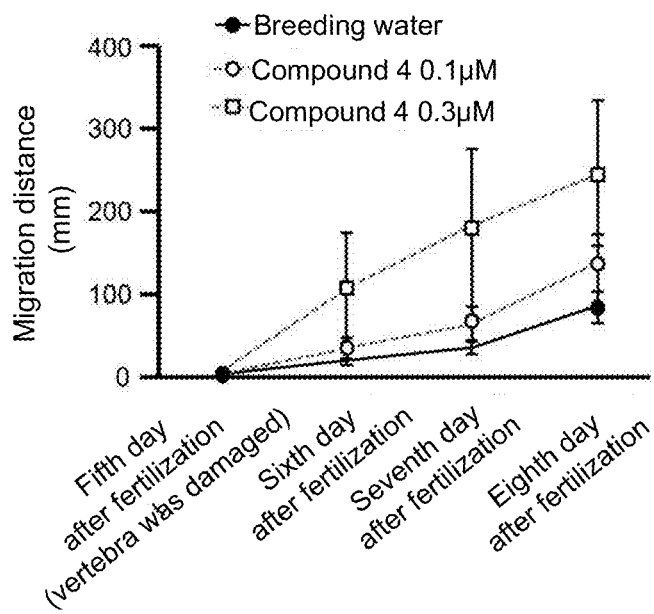
FIG. 10 is a graph showing examples of the results of behavior analysis made by measuring the distances that zebrafish have migrated after their spinal cord injury.

On the fifth day after fertilization, the zebrafish spinal cord was injured using an ophthalmic scalpel, and the zebrafish was bred in breeding water containing Compound 4 until the eighth day after fertilization. FIG. 10 shows the results of the migration distance measured by behavior analysis from the sixth day to eighth day after fertilization.

FIG. 10 is a graph of the migration distances of zebrafish after spinal cord injury measured by behavior analysis. It was observed that the migration distance was recovered due to Compound 4 being added to the breeding water. The results showed that Compound 4 was effective for a spinal cord injured model of a zebrafish.

Experimental Example 11: Effect of Compounds 4 and 10 on Stabilization of Cyclin D1

Figure 11A:
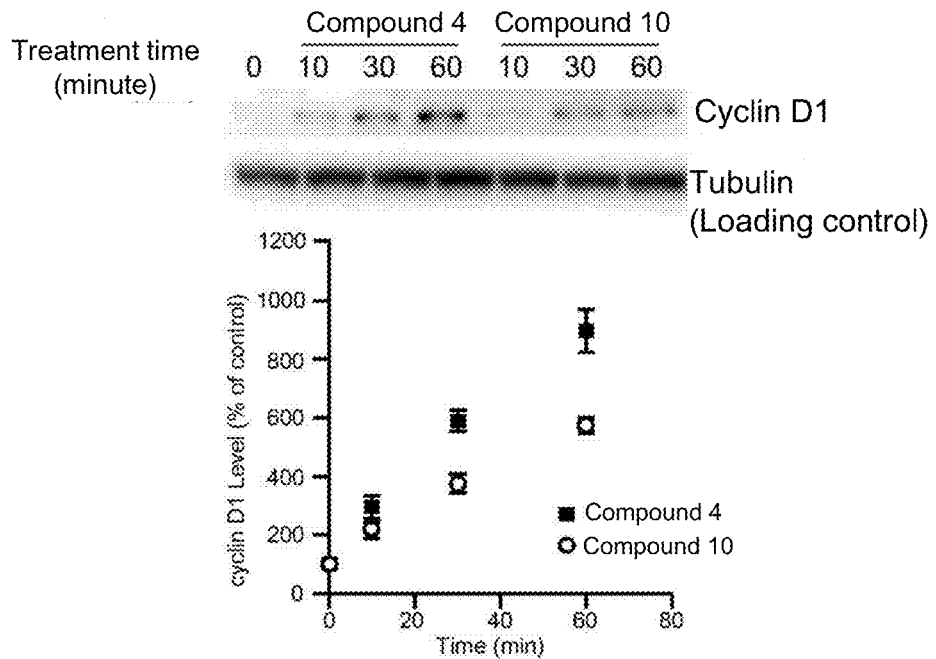
FIG. 11A is an example of the result of Western blotting showing the expression level of cyclin D1 in HEK293 cells treated with Compound 4 or 10 over time.

HEK293 cells were treated with Compound 4 or 10 over time, and the expression level of cyclin D1 was examined through Western blotting. FIG. 11A shows the results. As shown in FIG. 11A, the protein level of cyclin D1 increased (i.e. the cyclin D1 was stabilized) in a treatment time dependent manner.

Figure 11B:
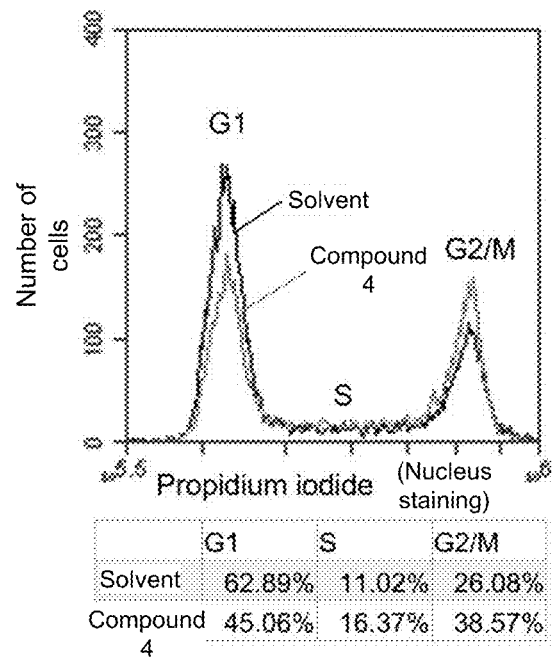
FIG. 11B is an example of the flow cytometry results showing the cell cycle of fibroblasts derived from human skin treated with a solvent or Compound 4 for 48 hours.

Next, fibroblasts derived from human skin were treated with a solvent or Compound 4 for 48 hours, and the cell cycle was analyzed through flow cytometry. FIG. 11B shows the results. As shown in FIG. 11B, the treatment of the cells with Compound 4 increased the ratio of cells in the G1 phase of the cell cycle decreased and the ratio of cell in the G2/M phase of the cell cycle. It is considered that this is because Compound 4 stabilized cyclin D1 and thus stimulated the progression of the cell cycle from the G1 phase to the subsequent S phase and G2/M phase.

The details of the mechanisms of the increase in the expression level of cyclin D1 (stabilization of cyclin D1) and the stimulation of the cell cycle as described above are not clear, but are presumed as follows. Cyclin D1 is expressed in the G1 phase of the cell cycle, and acts as a key molecule for the initiation of the cell cycle. In normal cells, the expression level of the cyclin D1 is suppressed due to the cyclin D1 being phosphorylated by DYRK1A and then decomposed by proteasome. On the other hand, it is thought that the decomposition of cyclin D1 is suppressed due to Compound 4 or 10 inhibiting the phosphorylation of cyclin D1, so that the expression level of cyclin D1 increases (cyclin D1 is stabilized), and as a result, the cell cycle is stimulated.

The invention claimed is:

1. A method for:
   treating a disease of the central nervous system and/or the peripheral nervous system, or
   treating a functional disorder of the central nervous system and/or the peripheral nervous system,
   wherein the method comprises administering, to a subject, a composition comprising, as an active ingredient, a compound having an ability to inhibit phosphorylation activity of a protein kinase or a prodrug thereof, or a pharmaceutically acceptable salt thereof,
   the compound is

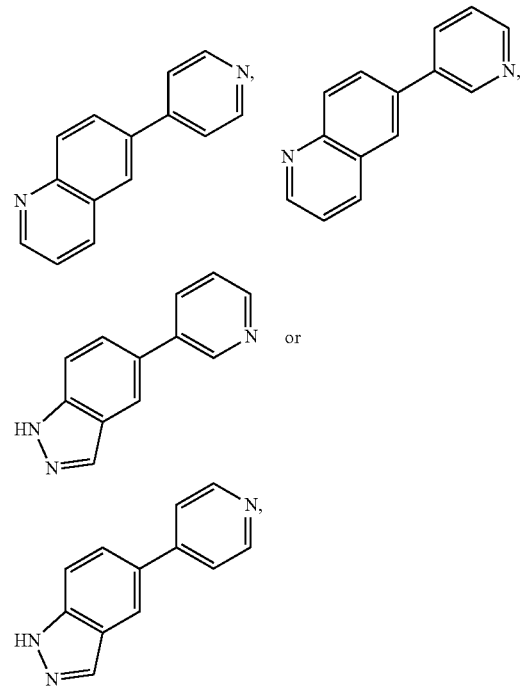

the disease of the central nervous system and/or the peripheral nervous system is Down syndrome, Alzheimer's disease or facial palsy, and
   the functional disorder of the central nervous system and/or the peripheral nervous system is a spinal cord injury.

2. The method according to claim 1, wherein the compound activates neurogenesis.

3. The method according to claim 1, wherein the protein kinase is at least one of DYRK and a cyclin D1 kinase.

* * * * *